(12) United States Patent
Blomquist et al.

(10) Patent No.: US 10,726,100 B2
(45) Date of Patent: Jul. 28, 2020

(54) DISPLAY FOR PUMP

(71) Applicant: Tandem Diabetes Care, Inc., San Diego, CA (US)

(72) Inventors: Michael L. Blomquist, Blaine, MN (US); Timothy B. Bresina, Shoreview, MN (US); Gail Beth Bynum, Brooklyn Park, MN (US); Michael D. Welsch, Stillwater, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 452 days.

(21) Appl. No.: 15/407,955

(22) Filed: Jan. 17, 2017

(65) Prior Publication Data

US 2017/0249443 A1    Aug. 31, 2017

Related U.S. Application Data

(60) Continuation of application No. 13/242,116, filed on Sep. 23, 2011, now abandoned, which is a division of
(Continued)

(51) Int. Cl.
*G09G 3/20* (2006.01)
*G09G 3/34* (2006.01)
(Continued)

(52) U.S. Cl.
CPC ....... *G06F 19/3468* (2013.01); *G09G 3/2003* (2013.01); *G09G 3/344* (2013.01);
(Continued)

(58) Field of Classification Search
CPC .............. G06F 3/04817; G06F 3/0482; G06F 3/04883; G06F 19/3468; A61M 2005/502; A61M 2005/14208
See application file for complete search history.

(56) References Cited

U.S. PATENT DOCUMENTS 2,968,804 A    1/1961    Buffington
3,555,286 A    1/1971    Cote
(Continued)

FOREIGN PATENT DOCUMENTS

CA    2060151    8/1992
CH    665955    6/1988
(Continued)

OTHER PUBLICATIONS

Invitation to Pay Additional Fees with Partial International Search for International Application No. PCT/US2007/017133 dated Feb. 27, 2008.
(Continued)

*Primary Examiner* — Quynh-Nhu H. Vu
(74) *Attorney, Agent, or Firm* — Patterson Thuente Pedersen, P.A.

(57) ABSTRACT

This document discusses, among other things, an apparatus comprising a pump configured to deliver insulin, a processor, and a user interface including a bistable display. A display element of the bistable display is placed in one of two stable orientations upon application of a biasing voltage and stays in the stable orientation when the biasing voltage is removed. The processor includes a display module configured to display a non-blank reversion display screen on the bistable display when no input is received at the user interface after a specified time duration, and to recurrently change the reversion display screen until input is received at the user interface.

15 Claims, 9 Drawing Sheets

Related U.S. Application Data application No. 12/114,033, filed on May 2, 2008, now Pat. No. 8,133,197.

(51) Int. Cl.
  *G06F 19/00* (2018.01)
  *G16H 40/63* (2018.01)
  *G16H 20/17* (2018.01)
  *G16H 50/30* (2018.01)

(52) U.S. Cl.
  CPC .......... *G09G 3/3466* (2013.01); *G16H 20/17* (2018.01); *G16H 40/63* (2018.01); *G16H 50/30* (2018.01); *G09G 2330/022* (2013.01); *G09G 2380/08* (2013.01)

(56) References Cited

U.S. PATENT DOCUMENTS

| | | |
|---|---|---|
| 3,603,152 A | 9/1971 | Alibert et al. |
| 3,777,165 A | 12/1973 | Bryant et al. |
| 3,809,871 A | 5/1974 | Howard et al. |
| 3,923,060 A | 12/1975 | Ellinwood, Jr. |
| 3,942,526 A | 3/1976 | Wilder et al. |
| 3,985,133 A | 10/1976 | Jenkins et al. |
| 4,027,536 A | 6/1977 | Heggie |
| T961,004 I4 | 8/1977 | Horton |
| 4,080,967 A | 3/1978 | O'Leary |
| 4,091,550 A | 5/1978 | Schrenk et al. |
| 4,098,267 A | 7/1978 | Stein et al. |
| 4,137,913 A | 2/1979 | Georgi |
| 4,141,252 A | 2/1979 | Lodge |
| 4,146,029 A | 3/1979 | Ellinwood, Jr. |
| 4,174,637 A | 11/1979 | Mulzet et al. |
| 4,184,815 A | 1/1980 | Casson et al. |
| 4,191,184 A | 3/1980 | Carlisle |
| 4,210,138 A | 7/1980 | Jess et al. |
| 4,213,454 A | 7/1980 | Shim |
| 4,217,993 A | 8/1980 | Jess et al. |
| 4,236,880 A | 12/1980 | Archibald |
| 4,270,532 A | 6/1981 | Frametzki et al. |
| 4,279,188 A | 7/1981 | Scott |
| 4,280,136 A | 7/1981 | Kasbima et al. |
| 4,282,872 A | 8/1981 | Franetzki et al. |
| 4,299,218 A | 11/1981 | Knigge et al. |
| 4,299,541 A | 11/1981 | Ohara et al. |
| 4,308,866 A | 1/1982 | Jelliffe et al. |
| 4,309,993 A | 1/1982 | Brown |
| 4,311,377 A | 1/1982 | Matteson |
| 4,314,227 A | 2/1982 | Eventoff |
| 4,314,228 A | 2/1982 | Eventoff |
| 4,315,238 A | 2/1982 | Eventoff |
| 4,320,757 A | 3/1982 | Whitney et al. |
| 4,368,645 A | 1/1983 | Glenn et al. |
| 4,369,780 A | 1/1983 | Sakai |
| 4,370,983 A | 2/1983 | Lichtenstein |
| 4,373,525 A | 2/1983 | Kobayashi |
| 4,373,527 A | 2/1983 | Fischell |
| 4,385,630 A | 5/1983 | Gilcher et al. |
| 4,385,958 A | 5/1983 | Long |
| RE31,315 E | 7/1983 | Jenkins et al. |
| 4,392,849 A | 7/1983 | Petre et al. |
| 4,394,862 A | 7/1983 | Shim |
| 4,395,259 A | 7/1983 | Prestele et al. |
| 4,396,977 A | 8/1983 | Slater et al. |
| 4,398,542 A | 8/1983 | Cunningham et al. |
| 4,410,322 A | 10/1983 | Archibald |
| 4,413,314 A | 11/1983 | Slater et al. |
| 4,425,661 A | 1/1984 | Moses et al. |
| 4,431,425 A | 2/1984 | Thompson et al. |
| 4,443,218 A | 4/1984 | DeCant, Jr. et al. |
| 4,446,344 A | 5/1984 | Fiedler |
| 4,460,355 A | 7/1984 | Layman |
| 4,484,479 A | 11/1984 | Eckhardt |
| 4,489,302 A | 12/1984 | Eventoff |
| 4,490,798 A | 12/1984 | Franks et al. |
| 4,493,704 A | 1/1985 | Beard et al. |
| 4,494,950 A | 1/1985 | Fischell |
| 4,498,843 A | 2/1985 | Schneider et al. |
| 4,512,013 A | 4/1985 | Nash et al. |
| 4,520,706 A | 6/1985 | Deforeit |
| 4,526,574 A | 7/1985 | Pekkarinen |
| 4,529,401 A | 7/1985 | Leslie et al. |
| 4,530,696 A | 7/1985 | Bisera et al. |
| 4,542,532 A | 7/1985 | McQuilkin |
| 4,534,756 A | 8/1985 | Nelson |
| 4,550,731 A | 11/1985 | Batina et al. |
| 4,550,748 A | 11/1985 | Nunez |
| 4,557,725 A | 12/1985 | Heyne et al. |
| 4,559,037 A | 12/1985 | Franetzki et al. |
| 4,559,038 A | 12/1985 | Berg et al. |
| 4,559,044 A | 12/1985 | Robinson et al. |
| 4,561,443 A | 12/1985 | Hogrefe |
| 4,562,751 A | 1/1986 | Nason et al. |
| 4,563,179 A | 1/1986 | Sakai |
| 4,565,542 A | 1/1986 | Berg |
| 4,578,573 A | 3/1986 | Flies et al. |
| 4,596,575 A | 6/1986 | Rosenberg et al. |
| 4,597,754 A | 7/1986 | Thill et al. |
| 4,601,702 A | 7/1986 | Hudson |
| 4,606,353 A | 8/1986 | Timm |
| 4,617,014 A | 10/1986 | Cannon et al. |
| 4,623,331 A | 11/1986 | Cewers et al. |
| 4,624,661 A | 11/1986 | Arimond |
| 4,627,835 A | 12/1986 | Fenton, Jr. |
| 4,627,839 A | 12/1986 | Young |
| 4,649,499 A | 3/1987 | Sutton et al. |
| 4,650,469 A | 3/1987 | Berg et al. |
| 4,652,260 A | 3/1987 | Fenton, Jr. |
| 4,656,603 A | 4/1987 | Dunn |
| 4,658,371 A | 4/1987 | Walsh et al. |
| 4,671,792 A | 6/1987 | Borsanyi |
| 4,676,776 A | 6/1987 | Hawson |
| 4,678,408 A | 7/1987 | Nason et al. |
| 4,681,563 A | 7/1987 | Deckert et al. |
| 4,685,903 A | 8/1987 | Cable et al. |
| 4,690,673 A | 9/1987 | Blomquist |
| 4,692,147 A | 9/1987 | Duggan |
| 4,696,671 A | 9/1987 | Epstein et al. |
| 4,710,163 A | 12/1987 | Butterfield |
| 4,714,462 A | 12/1987 | DiDomenico |
| 4,722,734 A | 2/1988 | Kollin |
| D294,733 S | 3/1988 | Peterson et al. |
| 4,731,051 A | 3/1988 | Fishell |
| 4,731,058 A | 3/1988 | Doan |
| 4,731,726 A | 3/1988 | Allen |
| 4,739,229 A | 4/1988 | Heiler et al. |
| 4,741,732 A | 5/1988 | Granshaw et al. |
| 4,745,301 A | 5/1988 | Michalchik |
| 4,747,828 A | 5/1988 | Tseo |
| 4,754,401 A | 6/1988 | Kaczynski et al. |
| 4,756,706 A | 7/1988 | Kerns et al. |
| 4,774,029 A | 9/1988 | Poulin |
| 4,775,368 A | 10/1988 | Iwatschenko |
| 4,778,449 A | 10/1988 | Weber et al. |
| 4,785,799 A | 11/1988 | Schoon et al. |
| 4,790,816 A | 12/1988 | Sundblom et al. |
| 4,799,381 A | 1/1989 | Tromp |
| 4,808,161 A | 2/1989 | Karmen |
| 4,808,167 A | 2/1989 | Mann et al. |
| 4,809,697 A | 3/1989 | Causey, III et al. |
| 4,810,243 A | 3/1989 | Howson |
| 4,810,992 A | 3/1989 | Eventoff |
| 4,816,019 A | 3/1989 | Karmen |
| 4,818,186 A | 4/1989 | Pastrone et al. |
| 4,826,810 A | 5/1989 | Aoki |
| 4,832,033 A | 5/1989 | Maher et al. |
| 4,836,752 A | 6/1989 | Burkett |
| 4,838,856 A | 6/1989 | Mulreany et al. |
| 4,838,857 A | 6/1989 | Strowe et al. |
| 4,842,584 A | 6/1989 | Pastrone |
| 4,846,792 A | 7/1989 | Bobo, Jr. et al. |
| 4,847,764 A | 7/1989 | Halvorson |
| 4,847,990 A | 7/1989 | Patrick |

(56) References Cited

U.S. PATENT DOCUMENTS

| | | |
|---|---|---|
| 4,850,807 A | 7/1989 | Frantz |
| 4,850,972 A | 7/1989 | Schulman et al. |
| 4,852,581 A | 8/1989 | Frank |
| 4,854,324 A | 8/1989 | Hirschman et al. |
| 4,856,339 A | 8/1989 | Williams |
| 4,863,425 A | 9/1989 | Slate et al. |
| 4,869,722 A | 9/1989 | Heyman |
| 4,871,351 A | 10/1989 | Feingold |
| 4,878,896 A | 10/1989 | Garrison et al. |
| 4,882,575 A | 11/1989 | Kawahara et al. |
| 4,889,132 A | 12/1989 | Hutcheson et al. |
| 4,898,578 A | 2/1990 | Rubalcaba, Jr. |
| 4,901,221 A | 2/1990 | Kodosky et al. |
| 4,908,017 A | 3/1990 | Howson et al. |
| 4,914,568 A | 4/1990 | Kodosky et al. |
| 4,918,930 A | 4/1990 | Gaudet et al. |
| 4,919,650 A | 4/1990 | Feingold et al. |
| 4,925,444 A | 5/1990 | Orkin et al. |
| 4,927,411 A | 5/1990 | Pastrone et al. |
| 4,933,873 A | 6/1990 | Kaufman et al. |
| 4,942,514 A | 7/1990 | Miyagaki et al. |
| 4,943,279 A | 7/1990 | Samiotes et al. |
| 4,950,235 A | 8/1990 | Slate et al. |
| 4,950,244 A | 8/1990 | Fellingham et al. |
| 4,954,818 A | 9/1990 | Naking et al. |
| 4,957,690 A | 9/1990 | Fennern |
| 4,961,533 A | 10/1990 | Teller et al. |
| 4,970,664 A | 11/1990 | Kaiser |
| 4,976,151 A | 12/1990 | Morishita |
| 4,978,335 A | 12/1990 | Arthur, III |
| 4,979,940 A | 12/1990 | Bobo, Jr. et al. |
| 4,994,035 A | 2/1991 | Mokros |
| 4,996,511 A | 2/1991 | Ohkawa et al. |
| 5,000,739 A | 3/1991 | Kulisz et al. |
| 5,006,997 A | 4/1991 | Reich |
| 5,009,641 A | 4/1991 | Gorton |
| 5,010,473 A | 4/1991 | Jacobs |
| 5,017,059 A | 5/1991 | Davis |
| 5,032,978 A | 7/1991 | Blomquist |
| 5,034,004 A | 7/1991 | Crankshaw |
| 5,038,800 A | 8/1991 | Oba |
| 5,041,086 A | 8/1991 | Koenig et al. |
| 5,047,014 A | 9/1991 | Mosebach et al. |
| 5,050,612 A | 9/1991 | Matsumura |
| 5,053,585 A | 10/1991 | Yaniger |
| 5,053,990 A | 10/1991 | Kreifels |
| 5,062,774 A | 11/1991 | Kramer et al. |
| 5,069,668 A | 12/1991 | Boydman |
| 5,074,756 A | 12/1991 | Davis |
| 5,078,682 A | 1/1992 | Miki et al. |
| 5,078,683 A | 1/1992 | Sancoff et al. |
| 5,082,014 A | 1/1992 | Olichney |
| 5,084,828 A | 1/1992 | Kaufman et al. |
| 5,087,245 A | 2/1992 | Doan |
| 5,088,983 A | 2/1992 | Burke |
| 5,096,385 A | 3/1992 | Georgi et al. |
| 5,098,262 A | 3/1992 | Wecker et al. |
| 5,098,409 A | 3/1992 | Stock |
| 5,100,380 A | 3/1992 | Epstein et al. |
| 5,103,211 A | 4/1992 | Daoud et al. |
| 5,104,374 A | 4/1992 | Bishko et al. |
| 5,111,234 A | 5/1992 | Taniguchi et al. |
| 5,115,223 A | 5/1992 | Moody |
| 5,116,312 A | 5/1992 | Blankenship et al. |
| 5,122,820 A | 6/1992 | Pagano et al. |
| 5,124,744 A | 6/1992 | Ogura et al. |
| 5,124,802 A | 6/1992 | Ito et al. |
| 5,131,816 A | 7/1992 | Brown et al. |
| 5,140,862 A | 8/1992 | Pappalardo |
| 5,153,827 A | 10/1992 | Coutre et al. |
| 5,154,700 A | 10/1992 | Danby |
| 5,155,693 A | 10/1992 | Altmayer et al. |
| 5,157,928 A | 10/1992 | Gaudlet et al. |
| 5,168,441 A | 12/1992 | Onarheim et al. |
| 5,172,698 A | 12/1992 | Stanko |
| 5,174,472 A | 12/1992 | Raque et al. |
| 5,176,004 A | 1/1993 | Gaudet |
| 5,181,910 A | 1/1993 | Scanlon |
| 5,190,442 A | 3/1993 | Jorritsma |
| 5,190,522 A | 3/1993 | Wojiciki et al. |
| 5,207,642 A | 5/1993 | Orkin et al. |
| 5,211,626 A | 5/1993 | Frank et al. |
| 5,213,573 A | 5/1993 | Sorich et al. |
| 5,217,355 A | 6/1993 | Hyman et al. |
| 5,219,327 A | 6/1993 | Okada |
| 5,221,268 A | 6/1993 | Barton et al. |
| 5,224,051 A | 6/1993 | Johnson |
| 5,230,623 A | 7/1993 | Guthrie et al. |
| 5,238,001 A | 8/1993 | Gallant et al. |
| 5,241,461 A | 8/1993 | Georges |
| 5,244,461 A | 9/1993 | Derlien |
| 5,244,463 A | 9/1993 | Cordner, Jr. et al. |
| 5,247,434 A | 9/1993 | Peterson et al. |
| 5,256,157 A | 10/1993 | Samiotes et al. |
| 5,265,431 A | 11/1993 | Gaudet et al. |
| 5,267,218 A | 11/1993 | Elbert |
| 5,291,190 A | 3/1994 | Scarola et al. |
| 5,295,062 A | 3/1994 | Fukshima |
| 5,301,301 A | 4/1994 | Kodusky et al. |
| 5,307,263 A | 4/1994 | Brown |
| 5,315,530 A | 5/1994 | Gerhardt et al. |
| 5,317,506 A | 5/1994 | Coutre et al. |
| 5,321,601 A | 6/1994 | Riedel et al. |
| 5,338,157 A | 8/1994 | Blomquist |
| 5,339,821 A | 8/1994 | Fujimoto |
| 5,350,411 A | 9/1994 | Ryan et al. |
| 5,353,316 A | 10/1994 | Scarola et al. |
| 5,354,273 A | 10/1994 | Hagen |
| 5,356,378 A | 10/1994 | Doan |
| 5,357,427 A | 10/1994 | Langen et al. |
| 5,363,482 A | 11/1994 | Victor et al. |
| 5,364,346 A | 11/1994 | Schrezenmeir |
| 5,368,562 A | 11/1994 | Blomquist et al. |
| 5,376,070 A | 12/1994 | Purvis et al. |
| 5,383,855 A | 1/1995 | Nicholson et al. |
| 5,386,360 A | 1/1995 | Wilson et al. |
| 5,388,202 A | 2/1995 | Squires et al. |
| 5,389,071 A | 2/1995 | Kawahara et al. |
| 5,389,078 A | 2/1995 | Zelesky et al. |
| 5,395,321 A | 3/1995 | Kawahara et al. |
| 5,400,246 A | 3/1995 | Wilson et al. |
| 5,412,400 A | 5/1995 | Takahara et al. |
| 5,429,602 A | 7/1995 | Hauser |
| 5,431,627 A | 7/1995 | Pastrone et al. |
| 5,432,709 A | 7/1995 | Vollweiler et al. |
| 5,440,585 A | 8/1995 | Patridge, III |
| 5,456,691 A | 10/1995 | Snell |
| 5,456,692 A | 10/1995 | Smith et al. |
| 5,478,211 A | 12/1995 | Dominiak et al. |
| 5,479,643 A | 12/1995 | Bhaskar et al. |
| 5,481,250 A | 1/1996 | Hano |
| 5,482,446 A | 1/1996 | Williamson et al. |
| 5,485,408 A | 1/1996 | Blomquist |
| 5,531,697 A | 7/1996 | Olsen et al. |
| 5,531,698 A | 7/1996 | Olsen |
| 5,537,436 A | 7/1996 | Bottoms et al. |
| 5,558,640 A | 9/1996 | Pfeiler et al. |
| 5,569,187 A | 10/1996 | Kaiser |
| 5,573,506 A | 11/1996 | Vasko |
| 5,582,593 A | 12/1996 | Hultman |
| 5,594,786 A | 1/1997 | Chaco et al. |
| 5,598,420 A | 1/1997 | Kaufman |
| 5,616,121 A | 4/1997 | McKay |
| 5,626,144 A | 5/1997 | Tacklind et al. |
| 5,630,710 A | 5/1997 | Tunc et al. |
| 5,643,212 A | 7/1997 | Coutre et al. |
| 5,647,854 A | 7/1997 | Olsen et al. |
| 5,658,250 A | 8/1997 | Blomquist et al. |
| 5,658,252 A | 8/1997 | Johnson |
| 5,660,176 A | 8/1997 | Iliff |
| 5,665,065 A | 9/1997 | Colman et al. |
| 5,669,877 A | 9/1997 | Blomquist |
| 5,681,285 A * | 10/1997 | Ford .................. A61M 5/172 604/151 |

(56) References Cited

U.S. PATENT DOCUMENTS

| | | | |
|---|---|---|---|
| 5,685,844 A | 11/1997 | Marttila | |
| 5,687,734 A | 11/1997 | Dempsey et al. | |
| 5,695,473 A | 12/1997 | Olsen | |
| 5,704,366 A | 1/1998 | Tacklind et al. | |
| 5,706,458 A | 1/1998 | Koppolu | |
| 5,717,603 A | 2/1998 | McClendon et al. | |
| 5,718,562 A | 2/1998 | Lawless et al. | |
| 5,719,761 A | 2/1998 | Gatti et al. | |
| 5,764,159 A | 6/1998 | Neftel | |
| 5,772,635 A | 6/1998 | Dastur et al. | |
| 5,781,442 A | 7/1998 | Engleson et al. | |
| 5,782,805 A * | 7/1998 | Meinzer | A61M 5/172 604/131 |
| 5,788,669 A | 8/1998 | Peterson | |
| 5,807,336 A | 9/1998 | Russo et al. | |
| 5,810,771 A | 9/1998 | Blomquist | |
| 5,814,015 A | 9/1998 | Gargano et al. | |
| 5,822,715 A * | 10/1998 | Worthington | G16H 50/50 702/19 |
| 5,836,989 A | 11/1998 | Shelton | |
| 5,857,967 A | 1/1999 | Frid et al. | |
| 5,861,018 A | 1/1999 | Feierbach | |
| 5,868,669 A | 2/1999 | Iliff | |
| 5,871,465 A | 2/1999 | Vasko | |
| 5,876,370 A | 3/1999 | Blomquist | |
| 5,879,143 A | 3/1999 | Cote et al. | |
| 5,879,163 A | 3/1999 | Brown et al. | |
| 5,885,245 A | 3/1999 | Lynch et al. | |
| 5,895,371 A | 4/1999 | Levitas et al. | |
| 5,897,493 A | 4/1999 | Brown | |
| 5,899,855 A | 5/1999 | Brown | |
| 5,913,310 A | 6/1999 | Brown | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,935,106 A | 8/1999 | Olsen | |
| 5,940,801 A | 8/1999 | Brown | |
| 5,956,501 A | 9/1999 | Brown | |
| 5,960,403 A | 9/1999 | Brown | |
| 5,966,691 A | 10/1999 | Kibre et al. | |
| 5,997,476 A | 12/1999 | Brown | |
| 6,012,034 A | 1/2000 | Hamparian et al. | |
| 6,024,539 A | 2/2000 | Blomquist | |
| 6,032,119 A | 2/2000 | Brown et al. | |
| 6,077,055 A | 6/2000 | Vilks | |
| 6,101,478 A | 8/2000 | Brown | |
| RE36,871 E | 9/2000 | Epstein et al. | |
| 6,241,704 B1 | 6/2001 | Peterson et al. | |
| 6,246,992 B1 | 6/2001 | Brown | |
| 6,248,067 B1 | 6/2001 | Mavity et al. | |
| 6,269,340 B1 | 7/2001 | Ford et al. | |
| 6,406,426 B1 | 6/2002 | Reuss et al. | |
| 6,422,057 B1 | 7/2002 | Anderson | |
| 6,475,180 B2 | 11/2002 | Peterson et al. | |
| 6,486,453 B1 * | 11/2002 | Bales | H05B 6/6435 219/400 |
| 6,551,276 B1 | 4/2003 | Mann et al. | |
| 6,554,798 B1 | 4/2003 | Mann et al. | |
| 6,558,320 B1 | 5/2003 | Causey, III et al. | |
| 6,641,533 B2 | 11/2003 | Causey, III et al. | |
| 6,671,563 B1 | 12/2003 | Engelson et al. | |
| 6,689,091 B2 | 2/2004 | Bui et al. | |
| 6,744,350 B2 | 6/2004 | Blomquist | |
| 6,749,586 B2 | 6/2004 | Vasko | |
| 6,765,877 B1 | 7/2004 | Foschiano et al. | |
| 6,809,653 B1 | 10/2004 | Mann et al. | |
| 6,852,104 B2 | 2/2005 | Blomquist | |
| 6,872,200 B2 | 3/2005 | Mann et al. | |
| 6,903,743 B2 | 6/2005 | Ng | |
| 6,904,434 B1 | 6/2005 | Wallach et al. | |
| 6,936,029 B2 | 8/2005 | Mann et al. | |
| 6,956,572 B2 | 10/2005 | Zaleski | |
| 6,979,326 B2 | 12/2005 | Mann et al. | |
| 6,997,920 B2 | 2/2006 | Mann et al. | |
| 6,999,854 B2 | 2/2006 | Roth | |
| 7,025,743 B2 | 4/2006 | Mann et al. | |
| 7,033,338 B2 | 4/2006 | Vilks et al. | |
| 7,036,089 B2 | 4/2006 | Bauer | |
| 7,041,082 B2 | 5/2006 | Blomquist et al. | |
| 7,042,643 B2 | 5/2006 | Miles | |
| 7,098,803 B2 | 8/2006 | Mann et al. | |
| 7,103,578 B2 | 9/2006 | Beck et al. | |
| 7,109,878 B2 | 9/2006 | Mann et al. | |
| 7,300,418 B2 | 11/2007 | Zaleski | |
| 7,324,012 B2 | 1/2008 | Mann et al. | |
| 7,347,836 B2 | 3/2008 | Peterson | |
| D570,363 S | 6/2008 | Ulm et al. | |
| D576,175 S | 9/2008 | Onodera | |
| D580,948 S | 11/2008 | Tomizawa et al. | |
| D586,351 S | 2/2009 | Gelman et al. | |
| D586,357 S | 2/2009 | Janinski | |
| D604,741 S | 11/2009 | DeBleser et al. | |
| 7,647,237 B2 | 1/2010 | Malave et al. | |
| 7,654,976 B2 | 2/2010 | Peterson et al. | |
| 7,689,939 B1 | 3/2010 | Becker | |
| 7,708,717 B2 | 5/2010 | Estes et al. | |
| 7,789,859 B2 | 9/2010 | Estes et al. | |
| 7,794,427 B2 | 9/2010 | Estes et al. | |
| 7,861,184 B2 * | 12/2010 | Kim | G06F 3/0482 715/811 |
| 8,133,197 B2 | 3/2012 | Blomquist et al. | |
| 8,881,102 B2 * | 11/2014 | Van De Sluis | G06F 3/033 717/120 |
| 2001/0031944 A1 | 10/2001 | Peterson et al. | |
| 2002/0033840 A1 * | 3/2002 | Masthoff | G06F 3/0482 715/700 |
| 2002/0107476 A1 | 8/2002 | Mann et al. | |
| 2002/0151804 A1 | 10/2002 | O'Mahony et al. | |
| 2002/0183693 A1 | 12/2002 | Peterson et al. | |
| 2002/0193679 A1 | 12/2002 | Malave et al. | |
| 2003/0011646 A1 | 1/2003 | Levine et al. | |
| 2003/0060765 A1 | 3/2003 | Campbell et al. | |
| 2003/0069650 A1 | 4/2003 | Karmiy et al. | |
| 2003/0114836 A1 | 6/2003 | Estes et al. | |
| 2003/0139701 A1 | 7/2003 | White et al. | |
| 2003/0144880 A1 | 7/2003 | Talachian et al. | |
| 2003/0145053 A1 | 7/2003 | Bodin | |
| 2003/0163088 A1 | 8/2003 | Blomquist | |
| 2003/0163223 A1 | 8/2003 | Blomquist | |
| 2003/0163789 A1 | 8/2003 | Blomquist | |
| 2003/0173408 A1 | 9/2003 | Mosher et al. | |
| 2003/0204413 A1 | 10/2003 | Riff | |
| 2003/0204415 A1 | 10/2003 | Knowlton | |
| 2003/0204416 A1 | 10/2003 | Sayeh et al. | |
| 2003/0212364 A1 | 11/2003 | Mann | |
| 2003/0212379 A1 | 11/2003 | Bylund et al. | |
| 2004/0010425 A1 | 1/2004 | Wilkes et al. | |
| 2004/0065321 A1 | 4/2004 | Stenzler | |
| 2004/0073095 A1 | 4/2004 | Causey, III et al. | |
| 2004/0158193 A1 | 8/2004 | Bui et al. | |
| 2004/0167465 A1 | 8/2004 | Mihai et al. | |
| 2004/0172302 A1 | 9/2004 | Martucci et al. | |
| 2004/0176984 A1 | 9/2004 | White et al. | |
| 2004/0249673 A1 | 12/2004 | Smith | |
| 2005/0001797 A1 | 1/2005 | Miller et al. | |
| 2005/0015731 A1 | 1/2005 | Mak et al. | |
| 2005/0055242 A1 | 3/2005 | Bello et al. | |
| 2005/0116023 A1 * | 6/2005 | Amundson | G05B 19/0426 235/376 |
| 2005/0137530 A1 | 6/2005 | Campbell et al. | |
| 2005/0144182 A1 | 6/2005 | Boris et al. | |
| 2005/0030164 A1 | 8/2005 | Mann et al. | |
| 2005/0171513 A1 | 8/2005 | Mann et al. | |
| 2005/0177395 A1 | 8/2005 | Blomquist | |
| 2005/0183037 A1 * | 8/2005 | Kuenzner | B60K 35/00 715/825 |
| 2005/0246416 A1 | 11/2005 | Blomquist | |
| 2006/0001550 A1 | 1/2006 | Mann et al. | |
| 2006/0026205 A1 | 2/2006 | Butterfield | |
| 2006/0041222 A1 | 2/2006 | Dewing et al. | |
| 2006/0079768 A1 * | 4/2006 | Small | A61M 5/14546 600/432 |
| 2006/0132292 A1 | 6/2006 | Blomquist | |

(56) References Cited

U.S. PATENT DOCUMENTS

| | | | |
|---|---|---|---|
| 2006/0202859 A1 | 9/2006 | Mastrototaro et al. | |
| 2006/0229557 A1 | 10/2006 | Fathallah et al. | |
| 2007/0100282 A1 | 5/2007 | Small et al. | |
| 2007/0129825 A1* | 6/2007 | Kargenian | G06F 19/00 700/83 |
| 2007/0156033 A1 | 7/2007 | Causey, III et al. | |
| 2007/0157089 A1* | 7/2007 | Van Os | G06F 3/04817 715/702 |
| 2007/0213657 A1 | 9/2007 | Jennewine et al. | |
| 2007/0255322 A1 | 11/2007 | Gerber et al. | |
| 2008/0005700 A1* | 1/2008 | Morikawa | G06F 3/0482 715/841 |
| 2008/0030369 A1 | 2/2008 | Mann et al. | |
| 2008/0033357 A1 | 2/2008 | Mann et al. | |
| 2008/0033360 A1 | 2/2008 | Evans et al. | |
| 2008/0033361 A1 | 2/2008 | Evans et al. | |
| 2008/0033402 A1 | 2/2008 | Blomquist | |
| 2008/0033749 A1 | 2/2008 | Blomquist | |
| 2008/0034323 A1 | 2/2008 | Blomquist | |
| 2008/0065007 A1 | 3/2008 | Peterson et al. | |
| 2008/0065016 A1 | 3/2008 | Peterson et al. | |
| 2008/0065926 A1* | 3/2008 | Poth | G05B 15/02 713/500 |
| 2008/0122796 A1* | 5/2008 | Jobs | G06F 3/0488 345/173 |
| 2008/0126969 A1 | 5/2008 | Blomquist | |
| 2008/0132844 A1 | 6/2008 | Peterson et al. | |
| 2008/0155415 A1* | 6/2008 | Yoon | G06F 3/016 715/716 |
| 2008/0189614 A1* | 8/2008 | Jeong | G06F 3/0482 715/716 |
| 2008/0300534 A1 | 12/2008 | Blomquist | |
| 2009/0177180 A1* | 7/2009 | Rubalcaba, Jr. | G06F 8/60 604/500 |
| 2009/0275886 A1 | 11/2009 | Blomquist et al. | |
| 2010/0020064 A1 | 1/2010 | Roosendaal et al. | |
| 2012/0013625 A1 | 1/2012 | Blomquist et al. | |
| 2012/0013802 A1 | 1/2012 | Blomquist et al. | |

FOREIGN PATENT DOCUMENTS

| | | |
|---|---|---|
| EP | 0069350 | 1/1983 |
| EP | 0078645 | 5/1983 |
| EP | 0183351 | 6/1986 |
| EP | 0188288 | 7/1986 |
| EP | 0221005 | 5/1987 |
| EP | 0233115 | 8/1987 |
| EP | 319272 | 6/1989 |
| EP | 0328162 | 8/1989 |
| EP | 0384155 | 8/1990 |
| EP | 408483 | 1/1991 |
| EP | 0497041 | 8/1992 |
| EP | 503670 | 9/1992 |
| EP | 0371507 | 3/1993 |
| EP | 551088 | 7/1993 |
| EP | 0806738 | 12/1997 |
| EP | 0952541 | 10/1999 |
| EP | 1587017 | 10/2005 |
| EP | 1647291 | 4/2006 |
| FR | 2603488 | 3/1988 |
| FR | 2675288 | 10/1992 |
| GB | 2039083 | 7/1980 |
| GB | 2262452 | 6/1993 |
| GB | 2312055 | 10/1997 |
| JP | 409192218 | 7/1997 |
| JP | 2002291706 | 10/2002 |
| WO | WO 8403218 | 8/1984 |
| WO | WO8703814 | 7/1987 |
| WO | WO8707161 | 12/1987 |
| WO | WO91/16609 | 10/1991 |
| WO | WO92/08647 | 5/1992 |
| WO | WO92/15439 | 9/1992 |
| WO | WO94/05355 | 3/1994 |
| WO | WO94/08647 | 4/1994 |
| WO | WO95/02426 | 1/1995 |
| WO | WO95/25893 | 9/1995 |
| WO | WO95/28190 | 10/1995 |
| WO | WO96/03168 | 2/1996 |
| WO | WO96/20745 | 7/1996 |
| WO | WO96/36389 | 11/1996 |
| WO | WO97/15227 | 5/1997 |
| WO | WO97/25083 | 7/1997 |
| WO | WO98/20439 | 5/1998 |
| WO | WO98/24358 | 6/1998 |
| WO | WO98/42407 | 10/1998 |
| WO | WO98/59487 | 12/1998 |
| WO | WO99/08183 | 2/1999 |
| WO | WO99/10801 | 3/1999 |
| WO | WO99/18532 | 4/1999 |
| WO | WO99/22236 | 5/1999 |
| WO | WO 00/48112 | 8/2000 |
| WO | WO0045696 | 8/2000 |
| WO | WO 0045696 A1 | 8/2000 |
| WO | WO 0152727 | 7/2001 |
| WO | WO02/11049 | 2/2002 |
| WO | WO03/053503 | 7/2003 |
| WO | WO03/094075 | 11/2003 |
| WO | WO 2005/056083 | 6/2005 |
| WO | WO 2005/083619 | 9/2005 |
| WO | WO2006/023636 | 3/2006 |
| WO | WO 2006/073400 | 7/2006 |
| WO | WO2008/019013 | 2/2008 |
| WO | WO2008/019014 | 2/2008 |
| WO | WO2008/019015 | 2/2008 |
| WO | WO2008016621 | 2/2008 |
| WO | WO2008/048587 | 4/2008 |
| WO | WO2008/019016 | 11/2008 |
| WO | WO2009/135108 | 11/2009 |

OTHER PUBLICATIONS

International Search Report for International Application No. PCT/US94/07582 dated Oct. 28, 1994.

Notification of Reasons for Refusal for Japanese Patent Application No. 2006-542752 dated Jun. 23, 2010.

Steinfeld,Internet-Appliance Technology Automates Test Equipment. pp. 157-169. Oct. 12, 2000.

Merritt, "Wireless Hospital Health Care Products on the Upswing". Jan. 7, 2004.

Steinfeld, Is Embedded Going Net-Crazy?? A Response. Internet Article Mar. 29, 2001.

International Search Report for International Application No. PCT/US2007/017122 dated Feb. 19, 2008.

Written Opinion for International Application No. PCT/US2007/017122 dated Feb. 19, 2008.

International Search Report for International Application No. PCT/US2005/005829 dated Nov. 10, 2005.

Written Opinion for International Application No. PCT/US2005/005829 dated Nov. 10, 2005.

International Search Report for International Application No. PCT/US2004/040397 dated Feb. 7, 2006.

Written Opinion for International Application No. PCT/US2004/040397 dated Feb. 7, 2006.

International Search Report for International Application No. PCT/US2007/017138 dated Nov. 20, 2007.

Written Opinion for International Application No. PCT/US2007/017138 dated Nov. 20, 2007.

International Search Report for International Application No. PCT/US2007/017123 dated Jan. 25, 2008.

Written Opinion for International Application No. PCT/US2007/017123 dated Jan. 25, 2008.

International Search Report for International Application No. PCT/US2007/017120 dated Jan. 25, 2008.

Written Opinion for International Application No. PCT/US2007/017120 dated Jan. 25, 2008.

European Office Action for European Application No. 05713999 dated Oct. 30, 2009.

International Search Report for International Application No. PCT/US2007/017133 dated May 8, 2008.

(56) References Cited

OTHER PUBLICATIONS

Written Opinion for International Application No. PCT/US2007/017133 dated May 8, 2008.
International Search Report for International Application No. PCT/US2007/022051 dated Mar. 7, 2008.
Written Opinion for International Application No. PCT/US2007/022051 dated Mar. 7, 2008.
Declaration of non-establishment of ISR for International Application No. PCT/US2009/042494 dated Jan. 5, 2010.
Written Opinion for International Application No. PCT/US2009/042494 dated Jan. 5, 2010.
European Office Action for European Application No. 07797060 dated Jul. 3, 2009.
European Office Action for European Application No. 07797060 dated Feb. 9, 2010.
European Office Action for European Application No. 07797060 dated Dec. 8, 2010.
Australian Office Action for Application No. 2004296794 dated Dec. 3, 2009.
Notification of Reasons for Refusal for Japanese Patent Application No. 2006-554321 dispatch date Apr. 19, 2010.
Decision of Refusal for Japanese Application No. 2006-554321 dispatch date Apr. 18, 2011.
Examiner's first report on Australian patent application No. 2005216321 by Smiths Medical ASD, INC dated Nov. 26, 2009.
Examiner's report No. 3 on patent application No. 2005216321 by Smiths Medical ASD Inc. dated Apr. 20, 2011, Australian Government IP.
Notification of Reasons for Refusal for Japanese Application No. 2006-542752 dispatch date Jun. 28, 2010.
Examiner's first report on patent application No. 2004296794 by Smiths Medical ASD, Inc. dated Dec. 3, 2009. Australian Government IP.
Examiner's report No. 2 on patent application No. 2005216321 by Smiths Medical ASD, Inc. dated Jan. 7, 2011. Australian Government IP.
Decision of Refusal for Japanese Application No. 2006-542752 dispatch date Jul. 4, 2011.
Australian Office Action dated May 10, 2012 for Australian Application No. 2007282068.
Canadian OA from Canadian Application No. 2552580 dated Sep. 5, 2012.
Application and File History for U.S. Appl. No. 29/306,071, filed Apr. 1, 2008, inventor DeBleser et al.
Application and File History for U.S. Appl. No. 10/087,449, filed Feb. 28, 2002, inventor Blomquist.
Application and File History for U.S. Appl. No. 11/702,925, filed Feb. 25, 2007, inventors Evans et al.
Application and File History for U.S. Appl. No. 11/066,425, filed Feb. 22, 2005, inventor Blomquist.
Application and File History for U.S. Appl. No. 11/003,147, filed Dec. 3, 2004, inventor Blomquist.
Application and File History for U.S. Appl. No. 11/499,255, filed Aug. 3, 2006, inventor Blomquist.
Application and File History for U.S. Appl. No. 11/702,922, filed Feb. 5, 2007, inventors Evan et al.
Application and File History for U.S. Appl. No. 11/499,893, filed Aug. 3, 2006, inventor Blomquist.
Application and File History for U.S. Appl. No. 11/499,248, filed Aug. 3, 2006, inventor Blomquist.
Application and File History for U.S. Appl. No. 11/499,240, filed Aug. 3, 2006, inventor Blomquist.
Application and File History for U.S. Appl. No. 11/981,788, filed Oct. 31, 2007, inventor Peterson et al.
Application and File History for U.S. Appl. No. 11/981,248, filed Oct. 31, 2007, inventor Peterson et al.
Application and File History for U.S. Appl. No. 10/087,205, filed Feb. 28, 2002, inventor Blomquist.
Application and File History for U.S. Appl. No. 12/114,033, filed May 2, 2008, inventors Blomquist et al.
Application and File History for U.S. Appl. No. 07/942,288, filed Sep. 9, 1992, inventor Blomquist.
Application and File History for U.S. Appl. No. 08/090,738, filed Jul. 13, 1993, inventor Blomquist See Application and File History for U.S. Appl. No. 08/555,304, filed Nov. 8, 1995, inventor Blomquist.
Application and File History for U.S. Appl. No. 08/206,737, filed Mar. 7, 1994, inventor Blomquist.
Application and File History for U.S. Appl. No. 08/276,025, filed Jul. 15, 1994, inventor Blomquist.
Application and File History for U.S. Appl. No. 08/540,960, filed Oct. 11, 1995, inventor Blomquist See Application and File History for U.S. Appl. No. 08/782,486, filed Jan. 10, 1997, inventor Peterson.
Application and File History for U.S. Appl. No. 08/555,304, filed Nov. 8, 1995, inventor Blomquist.
Application and File History for U.S. Appl. No. 08/561,809, filed Nov. 22, 1995, inventor Peterson.
Application and File History for U.S. Appl. No. 08/586,952, filed Jan. 16, 1996, inventor Blomquist See Application and File History for U.S. Appl. No. 08/782,486, filed Jan. 10, 1997, inventor Peterson.
Application and File History for U.S. Appl. No. 08/782,486, filed Jan. 10, 1997, inventor Peterson.
Application and File History for U.S. Appl. No. 08/800,477, filed Feb. 14, 1997 inventor Blomquist.
Application and File History for U.S. Appl. No. 08/868,913, filed Jun. 4, 1997, inventor Blomquist.
Application and File History for U.S. Appl. No. 08/934,875, filed Sep. 22, 1997, inventor Blomquist.
Application and File History for U.S. Appl. No. 08/978,779, filed Nov. 26, 1997, inventor Blomquist.
Application and File History for U.S. Appl. No. 09/324,305, filed Jun. 2, 1999, inventor Peterson.
Application and File History for U.S. Appl. No. 09/421,751, filed Oct. 20, 1999, inventor Blomquist.
Application and File History for U.S. Appl. No. 09/795,266, filed Feb. 27, 2001, inventor Peterson.
Application and File History for U.S. Appl. No. 10/068,291, filed Feb. 5, 2002, inventor Peterson.
Application and File History for U.S. Appl. No. 11/981,229, filed Oct. 31, 2007, inventor Peterson.
Application and File History for U.S. Appl. No. 13/242,045, filed Sep. 23, 2011, inventors Blomquist et al.
Application and File History for U.S. Appl. No. 13/242,116, filed Sep. 23, 2011, inventors Blomquist et al.
Examiner's first report No. 4 on Australian patent application No. 2005216321 dated Aug. 25, 2011.
Examiner's first report on Australian patent application No. 2007282069 dated Jul. 11, 2011.
Examiner's first report on Australian patent application No. 2007281512 dated Jul. 4, 2011.
Examiner's first report on Australian patent application No. 2007282071 dated Jul. 11, 2011.
Devices for Insulin Administration, Jean-Louis Selam, MD and M. Arthur Charles, MD, PhD., Diabetes Care, vol. 13, No. 9, Sep. 1990. pp. 955-979.
A Semi-closed loop computer-assisted insulin infusion system, Donald J. Chisholm, Edward W. Kraegen, David J. Bell and David R. Chipps, The Medical Journal of Australia, Dec. 8/22, 1984. pp. 13-17.
Hypertensive Crisis Managed by Computer-Controlled Infusion of Sodium Nitroprusside; A Model for the Closed-Loop Administration of Short-Acting Vasoactive Agents. Jeremy J. Hammond, Walter M. Kirkdendall, Richard V. Calfee, Comupters and Biomedical Research, vol. 12, pp. 97-108, 1979.
Computerized Continuous Infusion of Intravenous Anesthetic Drugs During Pediatric Cardiac Surgery; Kern FH, Ungerleider RM, Jacobs JR, Boyd JL 3rd, Reyes JG, Goodman D. Greeley WJ; Department of Anesthesiology, Duke Heart Center, Duke University Medical Center, Durham, North Carolina, Anesth Analg. Apr. 1991; 72(4): 487-92.

(56) References Cited

OTHER PUBLICATIONS

Use of a Microprocessor in the Control of Malignant Hypertension with Sodium Nitroprusside, Jackson RV, Love JB, Parkin WG, Wahlquist ML, Williams NS, Aust N Z J Med. Aug. 1977; 7(4):414-7.
Effective Control of Blood Pressure by Computerized Infusion of Sodium Nitroprusside, R.V. Calfee, J.J. Hammond, W.M. Kirkendall, Clinical Research, vol. 25, 1977.
Automated Patient Care Following Cardiac Surgery. Nicholas T. Kouchoukos; Louis B. Sheppard; John W. Kirklin, Cardiovascular Clinics, Bol. 3, pp. 110-120, 1971.
A Simulation Study on a Self-Tuning Portable Controller of Blood Glucose. Brunetti P, Cobelli C, Cruciani P, Fabietti PG, Filippucci F, Santeusanio F, Sarti E. Medical Pathology Institute, Bioengineering Laboratory. University of Perugia, Italy. Int. J. ArtifOrgans. Jan. 1993; 16(1):51-7.
A Semi-Closed Loop Computer-Assisted Insulin Infusion System. Hospital use for Control of Diabetes in Patients, Chisholm DJ, Kraegan EW, Bell DJ, Chipps DR, Med J. Aust. Dec. 8-22, 1984;141(12-13):784-9.
Patient-controlled Portable Insulin Infusion Pump in Diabetes, Jergen Bojsen, Thorsten Deckert, Klaus Kelendorf, and Birthe Lerup, Diabetes vol. 28 Nov. 1979. Cover page and pp. 974-979.
Block Medical: Growing awith Home Infusion Therapy, In Vivio, The Business and Medicine Report, Apr. 1991, 3 pages.
Abbot Literature, 37 pages, as submitted Jun. 29, 1998 in U.S. Appl. No. 08/868,913.
Baxter Literature for MultiPlex™ Series 100 Fluid Management System, 4 pages, as submitted Jun. 29, 1998 in U.S. Appl. No. 08/868,913.
Baxter Literature for Flo-Guard® 6201 Volumetric Infusion Pump, Copyright 1992, 2 pages.
Greg Sancoff. San Diego Executive, "A Better Mousetrap," Sep. 1989, 4 pages.
Blade-Citizen, "Entrepeneur takes Aim at Home Health Care Market," Dec. 31, 1989, 2 pages.
"Product Overview, Verifuse Ambulatory Infusion Pump." Block Medical Inc, dated Sep. 1990, 4 pages.
Peter Lord et al., "MinMed Technologies Programmable Implantable Infusion System," pp. 66-91, from Annals of the New York Academy of Sciences, Neurilogical Applications of Implanted Drug Pumps, Copyright 1988.
Dertouzos, M., "Communications, Computers & Net-works," Scietific American Sep. 1991, pp. 62-69.
Dehne, T., "PC-Based Data Acquisition and Intrumentation," Analytical Chemistry, vol. 62, No. 9, May 1, 1990. pp. 565A, 566A, 568A, 570A, 571A, 572A.
"Ally™ Ambulatory Frug Infusion System", Q-Life Systems Inc., 3 pages, as submitted Jun. 29, 1988 in U.S. Appl. No. 08/868,913.
Fundamentals of Interactive Computer Graphics, Foley et al., Mar. 1993, pp. 10, 11, 29-35.
Imed Status Infusion Management System literature, 6 pages, as submitted Jun. 29, 1988 in U.S. Appl. No. 08/868,913.
Linkens et al., Computer Control Systems and Pharmacological Drug Administration: A Survey, Journal of Medical Engineering & Technology, vol. 14, No. 2, Mar./Apr. 1990, pp. 41-54.
McCarthy, LH, Software Simulates Instrumentation Systems, Design News, May 21, 1990, pp. 72-73.
National Instruments Document entitled "Scientific Data Analysis," 16 pages, as submitted Jun. 29, 1988 in U.S. Appl. No. 08/868,913.
National Instruments Instrumentation Newsletter, Aug. 1990, 20 pages. vol. 2, No. 3.
National Instruments Instrumentation Newsletter, Feb. 1991, 20 pages. vol. 3, No. 1.
National Instruments Instrumentation Newsletter, May 1990, 18 pages. vol. 2, No. 2.
National Instruments Instrumentation Newsletter, Nov. 1990, 16 pages. vol. 2, No. 4.
National Instruments Lab Windows 2.0 materials, 6 pages, as submitted Jun. 29, 1988 in U.S. Appl. No. 08/868,913.
National Instruments Lab Windows 1.2 materials dated Oct. 1989, 5 pages.
Bedder, M. et al., "Cost Analysis of Two Implantable Narcotic Delivery Systems," Journal of Pain and Symptom Management. vol. 6, No. 6, Aug. 1991. pp. 368-373.
Principles and Guidelines in Software User Interface Design, Deborah J. Mayhew, Chapter 9 Dialog Sryles: Direct Manipulation, copyright 1992, 17 pages.
Advertisement from HERCO, "Are Control Rooms Obsolete? Dated Mar. 1971, 1 page and Advertisement from HERCO," Are Control Rooms Obsolete? Dated Mar. 1972, 1 page.
Electronics Feb. 1990 article entitled "Who Will Dominate the Desktop in the '90's?", 3 pages.
The Orange County Register No. 21, 1991 article entitled "Portable TV frees patients," 1 page.
Article by McMorris et al., "Are Process Control Rooms Obsolete?", Control Engineering dated Jul. 1971, pp. 42-47.
LabVIEW® User Manual, Jan. 1990 Edition, cover page and pp. 2-1 through 2-36.
National Instruments' 1991 catalog entitled "IEEE-488 and VXIbus Control, Data Acquisition, and Analysis," cover page and pp. 1-1 through 1-13, 1-38, 4-68 and 4-69.
Abbot Laboratories Blue Line System Life Care® Model 4 Series System brochure, copyright 1990, 16 pages.
Operator's Manual for a CADD-Micro™ Ambulatroy Infusion Pump Model 5400, front cover and pp. ii-vi, pp. 1-55 and two back cover pages, copyright 1990.
Instruction Manual entitled "Quick Start for Speakerphone XT SVD", copyright 1996.
Bio Tek Instruments, Inc. Products Catalog. 32 pages. Apr. 1992.
Intel® document entitled, 28F001BX-T/28F001BX-B 1M(128Kx8) CMOS Flash Memory, dated Mar. 1991, 28 pages.
Intel® document entitled, 28F008SA8MBIT (1MBITx) Flashtile™ Memory dated Mar. 1992, 28 pages.
Lahti W. et al., "Byte", pp. 311-318, Nov. 1990. "Store Data in a Flash".
"A Programmable Infusion Pump Controller," 30th Annual Conference on Engineering in Medicine and Biology, Nov. 5-9, 1977 in Los Angeles, California, 11 pages.
"IV700 Service Manual." Valleylab, Inc. Boulder Colorado; Sep. 1988.
Designing the User Interface, Ben Shneiderman, Chapter 5 Direct Manipulation, Oct. 1993, 56 pages.
Operator's Manual for a CADD-Micro® Ambulatory Infusion Pump Model 5900, front cover and pp. ii-vi and 1-84, copyright 1993.
Provider® One Instruction Manual, Pancretec, Inc. as submitted on May 18, 1998 in U.S. Appl. No. 08/782,486.
Sheppard, L.C., Computerbased Clinical Systems: Automation and Intergration, 39th Annual Conference on Engineering in Medicine and Biology, Baltimore, Maryland, Sep. 13-16, 1986, pp. 73-75.
Wilson R., "Integrated Circuits" of Computer Design, pp. 26-27, Jun. 1, 1989.
Zales, S et al., Microprocessors and Microsystems vol. 14, No. 8, pp. 543-549, Oct. 1990.
Intravenous propofol anaesthesia using a computerized infustion system, M. White and G.N.C. Kenny, Anaesthesia, 1990, vol. 45, pp. 204-209.
Health Devices, ECRI A Nonprofit Agency, vol. 17 No. 12, Dec. 1988.
Health Devices, ECRI A Nonprofit Agency, vol. 19 Nos. 3-4, Mar.-Apr. 1989.
Operator's Manual, Gemini® PC-1 Volumetric Infusion Pump/Controller imed® Aug. 16, 1990.
Model 929 Computer Controlled Volumetric Infusion Pump Operating Instructions imed® as submitted Feb. 28, 2008 in U.S. Appl. No. 11/981,788.
Pain Control Devices Gaining Acceptance, Will Expand-Analgesic Delivery Devices-Industry Overview, http://www.findarticles.com/articles/mi_m3498/is_n5_v55/ai_12257770, Sep. 29, 2004.

(56) References Cited

OTHER PUBLICATIONS

A Standard Microcomputer Linked to a Volume-Controlled Infusion Pump for Patient-Controlled Analgesia Research, Journal of Medical Engineering and Technology, G.W.A. Gillies, G.N.C. Kenny and C.S. McArdle, vol. 10, No. 2, Mar./Apr. 1986. pp. 55-57.
The P1073 Medical Information Bus, David F. Franklin and David V. Ostler (Oct. 1989).
Imed 980 Volumetric Infusion Pump Operator's Manual. 1992.
Improving Acute Care Use of Medical Device Data, Robert J. Kennelly, Chair, IEEE 1073 "Standard for Medical Device Communications" Committee, Eden Shores Consulting. 1992.
Health Devices, ECRI A Nonprofit Agency, Sep. 1991, vol. 20, No. 9.
Medtronic MiniMed Paradigm Link Owner's Guide, BD Logic, 2003.
M68HC11 E Series, HCMOS Microcontroller Unit, Motorola, Inc. 1993, 1996.
Health Devices, ECRI A Nonprofit Agency, Dec. 1989, vol. 18 No. 12.
Health Devices, ECRI A Nonprofit Agency, Dec. 1991, vol. 20 No. 12.
510 (k) Registration Documents for Registration of K87022 and K871728 (1987).
510 (k) Registration Documents for Registration of K863997 (1986).
Complaint for Patent Infringement (Exhibits 1-3); C.A. No. 03-776, *Medtronic Minimed, Inc. v. Deltec Inc., and Smiths Medical Ltd.* Aug. 5, 2003.
First Amended Complaint for Patent Infringement (Exhibits 1-3); C.A. No. 03-776, *Medtronic Minimed, Inc. v. Deltec Inc. Smiths Group North America Inc. and Smiths Medical Ltd.* Nov. 3, 2003.
Answer and Counterclaims of Smiths Medical Md. Inc. (Exhibits 1-5); C.A. 03-776, *Medtronic Minimed, Inc. v. Deltec Inc., Smiths Group North America, Inc. and Smiths Group Pic.* Nov. 17, 2003.
Joint Claim Construction Statement (Exhibits 1-2); C.A. No. 03-776, *Medtronic Minimed, Inc. v. Smiths Medical Md, Inc.* Certificate of service Feb. 4, 2005.
Expert Response of Anthony Storace on behalf of Defendant Counterclaimant Smiths Medical Md., Inc. to The Expert Report Submitted by jack Goldberg on behlaf of Plaintiff Medtronic Minimed (Exhibits B-J); C.A. No. 03-776, *Medtronic Minimed Inc. v. Smiths Medical Md, Inc.* Jan. 14, 2005.
Medtronic Minimed's Reply Brief in Support of it's Motion for Summary Judgment of Non-Infringement of Claims 6 and 11 of Smiths '704 Patent (Exhibits A-B), *Medtroni Minimed Inc. v. Smith Medical Md, Inc.* Mar. 4, 2005.
Medtronic Minimed's Reply Brief in Support of its Motion for Summary Judgment of Invalidilty of Claims 6 and 11 of Smiths '704 Patent (Exhibits A-B); C.A. No. 03-776, *Medtronic Minimed Inc. v. Smiths Medical MD, Inc.* Mar. 4, 2005.
Defendant Smiths Medical Md. Inc. S. Answering Brief Responding to Medtronic Minimed Inc.'s Claim Contruction Brief for U.S. Pat. No. 6,241,704, C.A. No. 03-776, *Medtronic Minimed Inc. V. Smiths Medical Md. Inc.* Feb. 25, 2005.
Declaration of Anthony C. Roth in Support of Defendant-Counterclaim Plantiff Smiths Medical Md, Inc. 's Response Brief to Medtronic Minimed, Inc.'s Claim Construction Brief of U.S. Pat. No. 6,241,704 (Exhibits A-H); C.A. No. 03-776, *Medtronic Minimed Inc. v. Smith Medical Md, Inc.* Feb. 25, 2005.
Defendant Smiths Medical Md, Inc. 's Brief in Opposition to Medtronic Minimed, Inc 's Motion for Summary Judgment of Invalidity of Claims 6 and 11 of Smiths Medical Inc. 's U.S. Pat. No. 6,241,704; C.A. No. 03-776, *Medtronic Minimed, Inc. v. Smiths Medical Md. Inc.* Feb. 28, 2005.
Declaration of Anthony C. Roth in Support of Defendant-Counterclaim Plaintiff Smiths Medical Md, Inc. 's Brief in Opposition to Medtronic Minimed Inc. 's Motion for Summary Judgment of invalidity of claims 6 and 11 of Smiths Medical Inc. 's U.S. Pat. No. 6,241,704 (Exhibits 1-7); C,A, No. 03-7769, *Medtronic Minimed Inc. v. Smiths Medical Md. Inc.* Feb. 28, 2005.
Expert Report of Jack Goldberg on behalf of Plaintiff Medtronic Minimed Pursuant to Fed R. Civ. P. 26(A)(2) (Exhibits A-F); C.A. No. 03-776, *Medtronic Minimed Inc. v. Smiths Medical Md. Inc.* Executed Dec. 15, 2004.
Opening Brief in Support of Defendant Smiths Medical, Inc.'s Propsed Claim Contructions for U.S. Pat. No. 6,241,704; U.S. Pat. No. 6,554,065 and U.S. Pat. No. 6,554,798 (Exhibits 1-20); C.A. No. 03-776, *Medtronic Minimed, Inc. v. Smiths Medical Md, Inc.* Feb. 4, 2005.
Memorandum Opinion: C.A. No. 03-776, *Medtronic Minimed, Inc. v. Smiths Medical Md. Inc.* Jun. 1, 2005.
Order: C.A. No. 03-776; *Medtronic Minimed Inc. v. Smiths Medical Md. Inc.* Jun. 1, 2005.
Memorandum Opinion (Summary Judgment of Infringement of U.S. Pat. No. 5,665,065 and U.S. Pat. No. 6,554,798), C.A. No. 03-776, *Medtronic Minimed Inc. v. Smiths Medical Md. Inc.* Jun. 16, 2005.
DVD-University of Maryland at College Park MD. Human-Computer Interaction Laboratory, Apr. 1991.
DVD-University of Maryland at College Park MD. Human-Computer Interaction Laboratory, Apr. 1992.

\* cited by examiner

DISPLAY FOR PUMP

RELATED APPLICATIONS

This application is a continuation of application Ser. No. 13/242,116 filed Sep. 23, 2011, which in turn is a division of application Ser. No. 12/114,033 filed May 2, 2008, now U.S. Pat. No. 8,133,197 issued Mar. 13, 2012, which is hereby fully incorporated herein by reference.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. It is desirable for an insulin pump to have features that make the pump more convenient or more effective for the patient to use.

OVERVIEW

This document discusses, among other things, devices and methods for assisting a diabetic person manage insulin therapy. A device example includes a pump configured to deliver insulin, a processor, and a user interface that includes a bistable display. A display element of the bistable display is placed in one of two stable orientations upon application of a biasing voltage. The display element stays in the stable orientation when the biasing voltage is removed. The processor includes a display module configured to display a non-blank reversion display screen on the bistable display when no input is received at the user interface after a specified time duration, and to recurrently change the reversion display screen until input is received at the user interface.

A method example includes providing a bistable display on a device having an insulin pump, reverting the display to a non-blank reversion display screen when no input is received at a user interface after a specified time duration, and recurrently changing the reversion display screen until input is received at the user interface.

This section is intended to provide an overview of subject matter of the present patent application. It is not intended to provide an exclusive or exhaustive explanation of the invention. The detailed description is included to provide further information about the subject matter of the present patent application.

DETAILED DESCRIPTION

Figure 1A:
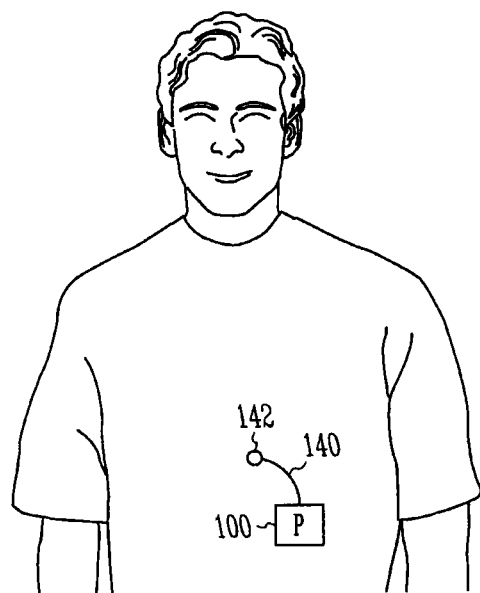
FIGS. 1A and 1B illustrate portions of a device that includes an insulin pump.
Figure 1B:
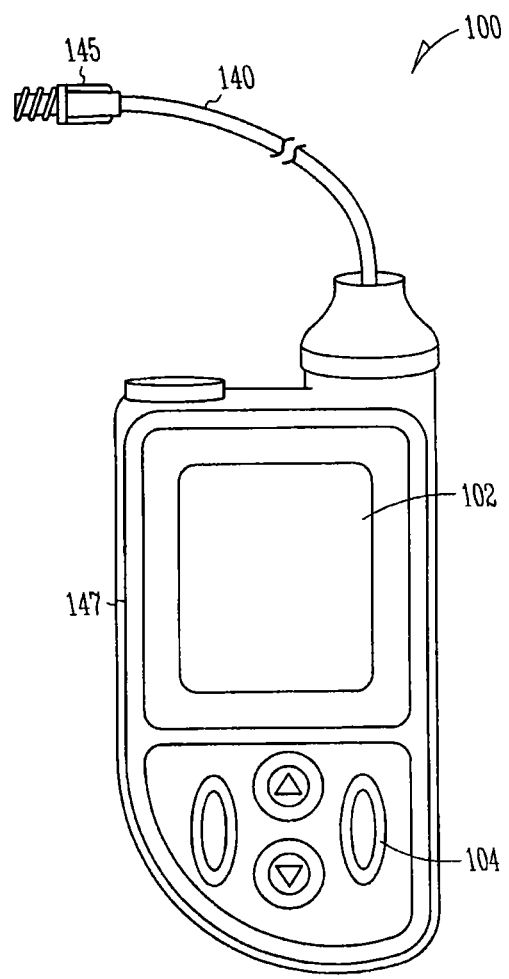

Insulin pump features may assist an insulin pump user in being more effective in treating their diabetes. FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104. Because proper use of an insulin pump often requires a user to go through a learning curve to properly treat their diabetes using the pump, it is desirable for a pump to provide assistance to the user in operating the pump, whether the user is a diabetic patient, a caregiver, or a clinician. Device displays are a useful way to provide information to the user.

Bistable Display

Ambulatory insulin pumps are typically battery powered. It is desirable to reduce power consumption in an ambulatory insulin pump device to extend the lifetime of the battery power source. Displays for the insulin pump devices typically require power to maintain the display. For example, organic light emitting diodes (OLEDs) require constant power source to generate light. Liquid crystal displays (LCDs) typically require a refresh cycle to periodically update the display. LCDs may also require backlighting to illuminate pixels of the display. These examples require power to maintain the display even if the information on the display does not change.

In a bistable display, a display element (e.g., a pixel or a subpixel) is placed in one of two stable orientations upon application of a biasing voltage, and the display element stays in the stable orientation when the biasing voltage is removed. Thus, a bistable display mainly requires power only when changing the orientation of the display element, and requires little or no power to maintain the orientation.

An example of a bistable display is an electrophoretic display (EPD). In an EPD, particles in the display acquire charge from the biasing voltage. The polarity of the voltage determines whether the charged particle will have a black appearance (the first stable orientation) or white appearance (the second stable orientation). Ambient reflected light is used to read the display similar to the way ambient light is used to read a newspaper. EPDs are sometime referred to as electronic paper (e-paper) or electronic ink (e-ink).

Another example of a bistable display is an interferometric modulator (IMOD) display. In some embodiments of an interferometric modulator display, application of a voltage causes a display element to have black appearance (the first stable orientation), and application of a lower voltage causes the display to appear bright and colored (the second stable state). In a bichrome display, the display element is a pixel and the bias voltage is applied to a pixel. In a color display, a color pixel is comprised of a grid of display elements called sub-pixels and the bias voltage is applied to a sub-pixel. The sub-pixels exhibit different colors when the lower voltage is applied and produce the same color (e.g., black) when the bias voltage is applied. Together, the sub-pixels provide a full color display using spatial dithering. A description of IMOD displays is found in U.S. Pat. No. 7,042,643, "Interferometric Modulation of Radiation," filed Feb. 19, 2002, which is incorporated herein in its entirety.

Because a bistable display requires little or no power to maintain the display, the display will likely appear the same whether the insulin pump is working or the insulin pump has malfunctioned. This may make it difficult for an insulin pump user to notice when the device has malfunctioned.

Figure 2:
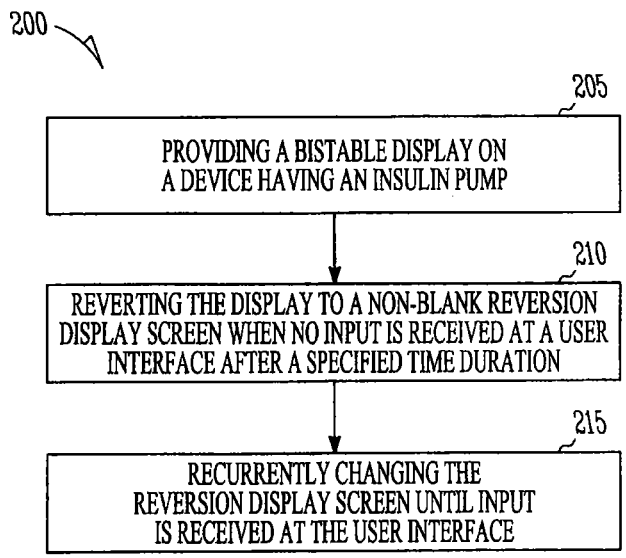
FIG. 2 is a flow diagram of a method of presenting an insulin pump display to a user.

FIG. 2 is a flow diagram of a method 200 of presenting an insulin pump display to a user. At block 205, a bistable display is provided on a device having an insulin pump. The display is bistable because a display element (e.g., a pixel or sub-pixel) may be placed in one of two stable orientations upon application of a biasing voltage, and the display element stays in the stable orientation when the biasing voltage is removed.

At block 210, the bistable display reverts to a non-blank reversion display screen when no input is received at a user interface of the insulin pump device after a specified time duration. For example, the reversion screen may be an icon from the manufacturer or a photo the user downloads into the insulin pump device. However, because of the nature of a bistable display, a user would not be able to notice from a simple reversion screen whether the device is still functioning properly.

At block 215, the reversion display screen is recurrently changed until input is received at the user interface. In some embodiments, recurrently changing the reversion display screen may include recurrently changing from one of a plurality of reversion display screens to another of the plurality of display screens. In some embodiments, recurrently changing the reversion display screen may include recurrently producing an animated effect on a single reversion display screen. In some embodiments, recurrently changing the reversion display screen may include switching among several display screens to create an animated effect, such as sequentially displaying animation frames to produce an animated effect. Use of reversion screens may assist a user in operating their insulin pump device.

Figure 3:
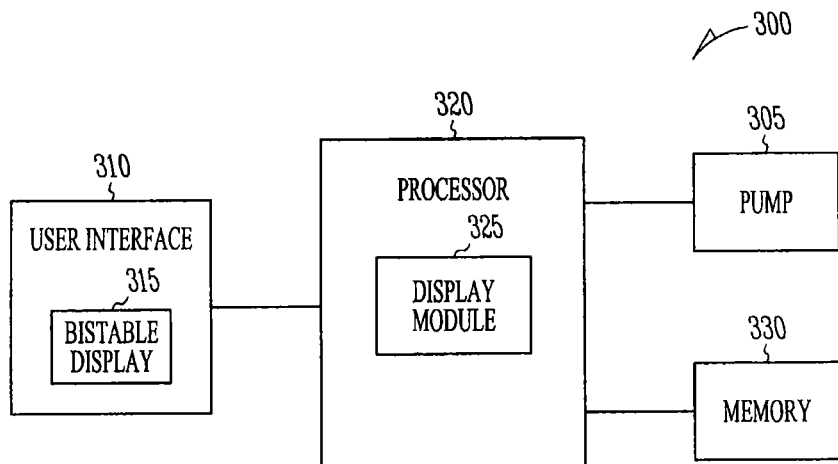
FIG. 3 is a block diagram of portions of an embodiment of an insulin pump device.

FIG. 3 is a block diagram of portions of an embodiment of an insulin pump device 300. The insulin pump device 300 includes a pump 305 configured to deliver insulin and a user interface 310. The pump 305 may be a positive displacement pump. Descriptions of an example of a medication pump to deliver insulin are found in Vilks et al., "Cartridge and Rod for Axially Loading a Medication Pump," U.S. Pat. No. 7,033,338, filed Feb. 28, 2002, which is incorporated herein by reference in its entirety. The pump 305 may drive a plunger in a removable insulin cartridge to deliver the insulin.

The user interface 310 includes a bistable display 315. In some embodiments, the bistable display 315 includes an interferometric modulation display. In some embodiments, the bistable display 315 includes an electrophoretic display. In some embodiments, the bistable display 315 includes an EPD. The substrate for the EPD may be made of flexible plastic. This provides a robust and thin display for the insulin pump device 300.

The insulin pump device 300 also includes a processor 320. The processor 320 may be a microprocessor, digital signal processor (DSP), or other type of processor. The processor 320 is configured to perform or execute a function or functions. Such functions correspond to modules to provide features integral to the first device. Modules may be software, hardware, firmware or any combination thereof. Multiple functions may be performed in one or more modules. In some embodiments, software or firmware is provided on a computer readable medium. The computer readable medium includes instructions therein, which when processed (such as by the processor 320 for example) results in a device performing the functions described herein. Examples of a computer readable medium include a compact disc (CD), memory stick, or remote storage accessible via a communication network such as the internet or a cell phone network.

The processor 320 is communicatively coupled to the pump 305 and the user interface 310. The communicative coupling allows the processor 320 to exchange electrical signals with the pump 305 and the user interface 310 even though intervening circuitry may be present. The processor 320 includes a display module 325 configured to display a non-blank reversion display screen on the bistable display 315 when no input is received at the user interface 310 after a specified time duration, and to recurrently change the reversion display screen until input is received at the user interface.

In some embodiments, the display module 325 is configured to produce an animated effect on the reversion display screen. For example, the animated effect may be a moving icon. The display module 325 recurrently produces the animated effect on the reversion display screen until input is received at the user interface 310. At which point the display module 325 may change from the reversion screen display to a home menu display.

In an illustrative example, the moving icon may be a clock and the animated effect may be moving hands of the clock.

The display module 325 periodically produces the animated effect by moving the hands of the clock to display time according to a timer of the processor. In some embodiments, the display module 325 is configured to display time on the reversion display screen by displaying numbers on the display screen and updating the numbers according to the time.

According to some embodiments, the insulin pump device 300 includes a memory 330 communicatively coupled to the processor 320. The memory 330 stores a plurality of reversion display screens, and the display module 325 is configured to display one of the plurality of reversion display screens when no input is received at the user interface after a specified time duration, and to recurrently change the reversion display screen from one of the plurality of reversion display screens to another of the plurality of reversion display screens while no input is received at the user interface 310. The reversion display screen would change after a time duration, such as every few seconds for example.

In some embodiments, the display module 325 is configured to change the reversion display screen in response to input received via the user interface. For example, as a test to verify the insulin pump device 300 is working properly, the reversion display screen would change when the user presses a specified user interface key or button. In another example, the user may use the user interface 310 to advance through several reversion display screen options and indicate a desired display screen. In certain embodiments, the memory 330 stores an indication that a reversion display screen is selected by a user. The display module 325 only displays one or more reversion screens selected by the user. In certain embodiments, one or more reversion screens are images downloaded by the user, such as photos for example. The display module 325 may display the images in a slide-show fashion.

Various events may cause the display module 325 to change the bistable display 315 from a reversion screen. In some embodiments, the display module 325 changes the bistable display 315 from the reversion display screen to a home menu when input is received at the user interface 310. In some embodiments, the display module 325 changes the bistable display 315 from the reversion display screen in response to a change in status of the insulin pump device 300. For example, the change in status may be related to a problem of the insulin pump device 300, such as an insulin cartridge containing less than a threshold level of insulin, a device battery having a capacity less than a threshold battery capacity value, or an indication that the insulin pump device is not operating correctly. The display module 325 may change to an alarm display screen to indicate a problem to the user, may change to a debug display screen to help the user determine the problem, or may display both an alarm display screen and a debug display screen.

In some embodiments, the display module 325 changes the reversion display screen in response to a detected change in a clinical status of a user. The change in clinical status may include at least one of a recent blood glucose reading being higher than a first threshold blood glucose value, a recent blood glucose reading being lower than the same threshold blood glucose value or a second threshold blood glucose value, the user exercising within a specified time period, the user eating within a specified time period, the user not eating within a specified time period, or the user having active insulin in their body. The display module 325 may change to an alarm display screen to indicate the change in clinical status to the user.

Custom Display Menus

Insulin pumps may be able to provide a variety of therapies and diagnostics for the user. Accessing the functions of the device may include navigating through several layers of device menus. It would be helpful to the user if the display menus are customized for the user. The menus may be automatically customized according to which functions are used most often, according to which functions are more appropriate for the users clinical status, or the menus may be manually customized by the user directly.

Figure 4:
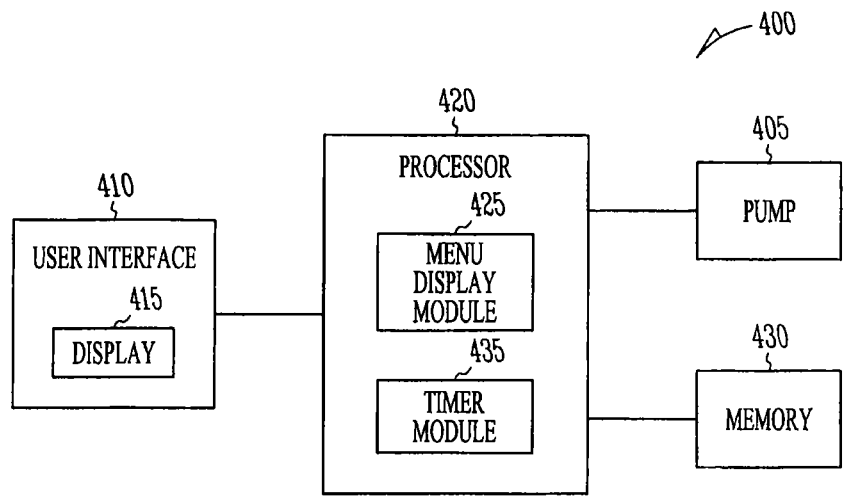
FIG. 4 is a block diagram of portions of another embodiment of an insulin pump device.

FIG. 4 is a block diagram of portions of an embodiment of an insulin pump device 400. The insulin pump device 400 includes a pump 405 configured to deliver insulin and a user interface 410 that includes a display 415. In some embodiments, the display 415 is a bistable display. The insulin pump device 400 also includes a processor 420 communicatively coupled to the pump 405 and the user interface 410. The processor 420 includes a menu display module 425. The menu display module 425 presents one of a plurality of device menus on the display 415.

Figure 5:
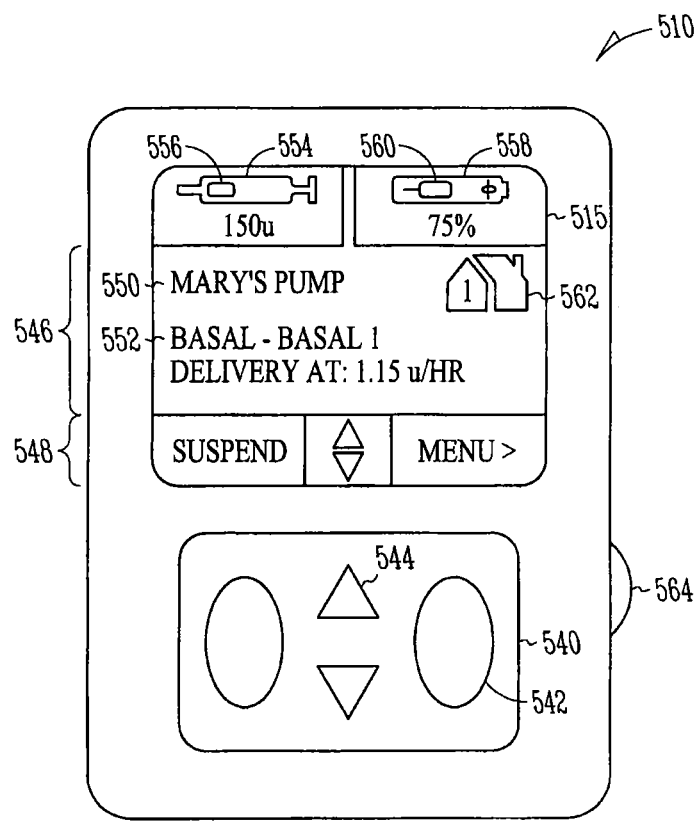
FIG. 5 shows an illustration of an example user interface with a display screen.

FIG. 5 shows an illustration of an example user interface 510 with a display screen 515. The user interface 510 includes a keypad 540 including function keys 542 and scroll keys 544 or up/down keys. The display screen 515 shows an example display menu having menu items. The user interface 510 receives a selection of a menu item included in a display menu. Selecting a menu item causes the processor to perform an action, such as indicating a status of the insulin pump device, modifying an operation parameter, or initiating a device task.

The example display menu shown has a top portion 546 and a bottom portion 548. The top portion 546 may show a display banner 550 identifying the pump as "Mary's Pump". The display banner 550 may be customized by the user via the keypad 540. The example display menu is one shown during active delivery of basil insulin. The display menu indicates basal insulin is being delivered at a rate of 1.15 units/hour according to a first basal schedule. The top portion 546 may present the name 552 of the active function and details of the function performed.

The bottom portion indicates the current function of the keys 542, 544. In the display shown, the pressing the left function key suspends the basal delivery. If delivery is suspended, the function of the left function key may change to activating the delivery. The right function key advances the display screen to a different display menu. The up/down keys retain the up/down function. For example, the scroll keys 544 may be used to highlight the name 552 of the active function in order to change from the first basal schedule.

The example display menu also shows a first icon 554 and a bar 556 to show the amount of insulin remaining in the insulin cartridge, and a second icon 558 and a bar 560 to indicate the remaining battery life. The example display menu also shows a third icon 562 to identify the display menu as the home menu or home page for the user.

Returning to FIG. 4, it was noted that the menu display module 425 presents one of a plurality of device menus on the display 415. The menu display module 425 arranges the device menus into an order for presentation according to user preference information. In some embodiments, the user preference information includes the frequency that certain menus are used. The menu display module 425 tracks device menu selections made via the user interface 410. The menu display module 425 then arranges the device menus into a presentation order according to a frequency with which device menus are used. For example, if the user frequently accesses the basal delivery display menu, the menu display module 425 moves the basal delivery display menu closer to the beginning of the order with which device menus are displayed.

According to some embodiments, the user preference information includes information regarding the clinical status of the user. The information may be entered into a memory 430 of the device via the user interface 410 or may be downloaded into the memory 430 via a communication port. The processor 420 receives the clinical status information and the menu display module 425 arranges the device menus into the presentation order according to the clinical status information.

For example, the clinical status information may indicate that the user has delayed gastric emptying. A user with delayed gastric emptying may use an extended or combination bolus of insulin. Descriptions of insulin pump devices that provide extended and combination boluses are found in Blomquist, U.S. patent application Ser. No. 11/679,712, "Carbohydrate Ratio Test Using Frequent Blood Glucose Input," filed Feb. 27, 2007, which is incorporated herein by reference in its entirety. The menu display module 425 may make it more convenient for the user to access the display menu used to program and initiate an extended and/or combination bolus (e.g., the extended bolus menu may be presented before the standard bolus display menu).

In another example, the clinical status information may include an indication that the user has a high or low blood glucose reading. The menu display module 425 may make it more convenient (e.g., displayed sooner in a hierarchy) for the user to access a display menu that is used when measuring blood glucose. The menu display module 425 may also make it more convenient for the user to access the blood glucose measurement display menu if the user is performing basal rate testing. Descriptions of devices that automatically perform basal rate testing are found in Blomquist, U.S. patent application Ser. No. 11/685,617, "Basal Rate Test Using Frequent Blood Glucose Input," filed Mar. 13, 2007, which is incorporated herein by reference in its entirety.

According to some embodiments, the processor 420 determines information regarding eating times of the user. The processor 420 may determine the information by receiving the information through a communication port or via a user interface. The processor 420 may determine the information by deducing the information regarding eating times from other programmed parameters, such as programmed meal boluses or programmed missed meal bolus alarms. In some embodiments the processor 420 may determine the information by learning the eating times of the user, such as by tracking the times a meal bolus is initiated for example.

The menu display module 425 arranges the device menus into the presentation order according to the eating times of the user. For example, based on the information, the menu display module 425 may arrange the display menus in anticipation of the user initiating a post-prandial blood glucose test, and make the blood glucose measurement display menu more convenient for the user to access.

According to some embodiments, the processor 420 includes a timing module 435. The menu display module 425 arranges the device menus into the presentation order according to a time of day. For example, the menu display module 425 may make it more convenient for the user to access a display menu used to program and/or initiate a meal or correction bolus based on time the user typically exercises or eats. In another example, if the user checks their blood glucose at a specific time of day, the menu display module 425 may make the blood glucose measurement display menu more convenient for the user to access at those times. In still another example, the user may disconnect the pump or change the insulin cartridge at specific times of day. The menu display module 425 may make the related display menus easier for the user to access at those times.

In some embodiments, the user enters the user preference information via the user interface. For example, the user enters an indication of which display menu she wishes to display as the home display menu. The processor 420 receives the user preference information and the menu display module 425 arranges the device menus into the presentation order according to the received user preference information.

The menu items included in a home menu are a subset of all available menu items. In some embodiments, the menu display module includes menu items in the home menu according to the user preference information. For example, the user may provide, via the user interface 410, an indication that the battery icon of FIG. 5 should be placed in the home menu. In certain embodiments, the processor 420 includes the timing module 435 and the user preference information includes a display reversion time duration. The menu display module 425 reverts from a displayed menu to the home menu when no displayed menu items are selected during the display reversion time duration.

In some embodiments, the menu display module 425 tracks device menu selections made via the user interface. The menu display module 425 includes menu items in the device home menu according to a frequency with which menu items are used. For example, if the user frequently checks how much insulin is remaining in the insulin cartridge, the menu display module 425 adds the insulin remaining icon to the home menu.

According to some embodiments, the insulin pump device 400 includes a memory 430 communicatively coupled to the processor to store a database of food options in association with a known amount of nutrient content. Nutrient content includes one or more of the amount of carbohydrates, fat, protein, or fiber in an amount of a type of food. The menu display module 425 displays food options in one or more display menus. The user indicates the food she is going to eat and the processor 420 may use the nutrient content for the indicated food option to determine an amount of insulin in a meal bolus or to determine a type of meal bolus for the user.

In some embodiments, the menu display module 425 is configured to track selections from the food database made by the user. The menu display module 425 may than arrange a viewing order of entries in the food database according to a frequency with which entries are selected. For example, if the user often selects pizza for lunch, the menu display module 425 may select that food option first when the food database menu is accessed at lunchtime.

In some embodiments, the user interface 410 includes a programmable tactile switch or button (e.g., tactile switch 564 in FIG. 5). The processor 420 is configured to initiate an action upon activation of the tactile switch. The processor action is specified in the user preference information. Thus, the tactile switch may be a generic switch or button until it is programmed by the user. For example, the tactile switch may be programmed to initiate a type of insulin bolus, to bring a specific display menu, or to activate a type of alarm provided by the insulin pump device 400.

Figure 6:
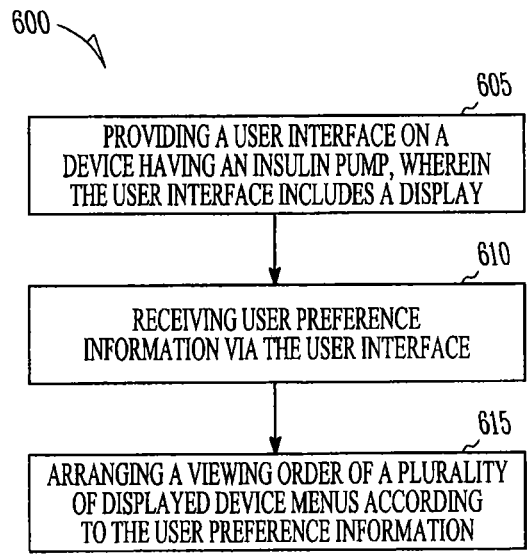
FIG. 6 is a flow diagram of another method of presenting an insulin pump display to a user.

FIG. 6 is a flow diagram of a method 600 of presenting an insulin pump display to a user. At block 605, a user interface is provided on a device having an insulin pump. The user interface includes a display. At block 610, user preference information is received into the device via the user interface.

At block 615, a viewing order of a plurality of displayed device menus is arranged according to the user preference information.

Color Display

Information presented on a display is not of much use to the user if the user does not notice the information. Color on a display can be used to bring a user's attention to a change in status of the device or a detected change in status of the patient.

Figure 7:
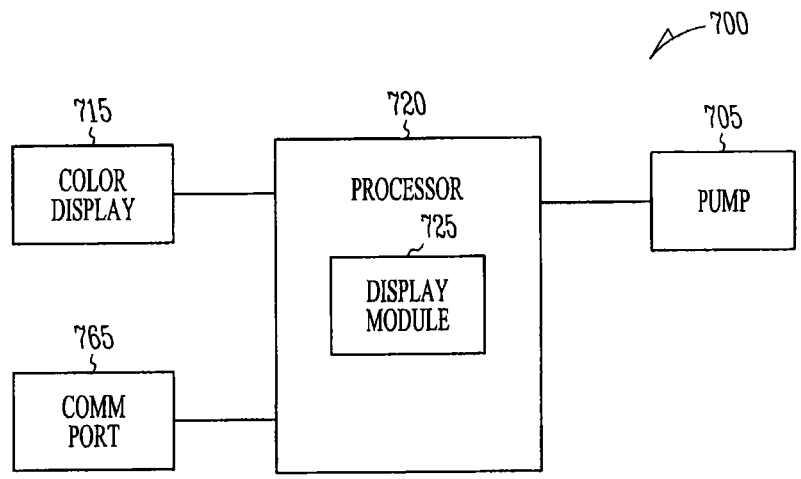
FIG. 7 is a block diagram of portions of an embodiment of an insulin pump device.

FIG. 7 is a block diagram of portions of an embodiment of an insulin pump device 700. The insulin pump device 700 includes a pump 705 configured to deliver insulin and a color display 715. In some embodiments, the color display 715 includes a color bistable display. The insulin pump device 700 also includes a processor 720 that comprises a display module 725 to display information related to clinical status of a user using a color indication and to change the color indication in response to a change in clinical status of the user.

Examples of a change in clinical status of the user include, among other things, a recent blood glucose reading being higher than a first threshold blood glucose value, a recent blood glucose reading being lower than the same threshold blood glucose value or a second threshold blood glucose value, the user exercising within a specified time period, the user eating within a specified time period, the user not eating within a specified time period, and the user having active insulin in their body.

Examples of change in a color indication used in the display 715 include, among other things, a change in a display background color, a change in a display backlight color, a change in a text color, and a color flashing indicator. The display module 725 changes the color indication when the clinical status changes. For example, the display module 725 may use a first display color when the user selects an insulin bolus display menu and there is no active insulin in the user's body, and uses a second display color when the user selects an insulin bolus display menu and there is active insulin in the user's body. In another example, the display module 725 may flash the insulin bolus display menu with the first or second display color when there is active insulin in the user's body.

In another embodiment, the change in a color indication is a gradual change. For example, the display module 725 may gradually change the color indication according to an amount of insulin that is active in the user, such as by gradually fading from the second display color to the first display color as the amount of active insulin decreases.

According to some embodiments, the display module 725 generates a device report on the color display 715. The processor 720 stores events in a memory integral to or communicatively coupled to the processor 720. The events may include historical insulin delivery information, recorded use parameters, and changes in the clinical status of the user. The display module 725 displays the device report and uses a color indication to show a change in clinical status.

In some embodiments, the insulin pump device includes a communication port 765 communicatively coupled to the processor 720. In some embodiments, the communication port 765 is a wireless port, such as an infrared (IR) port or a radio frequency (RF) port for example. In some embodiments, the communication port 765 is a wired port, such as a serial port for example. The processor 720 communicates the generated device report to a second separate device via the communication port, such as for printing of the device report or for displaying the device report for example.

Figure 8:
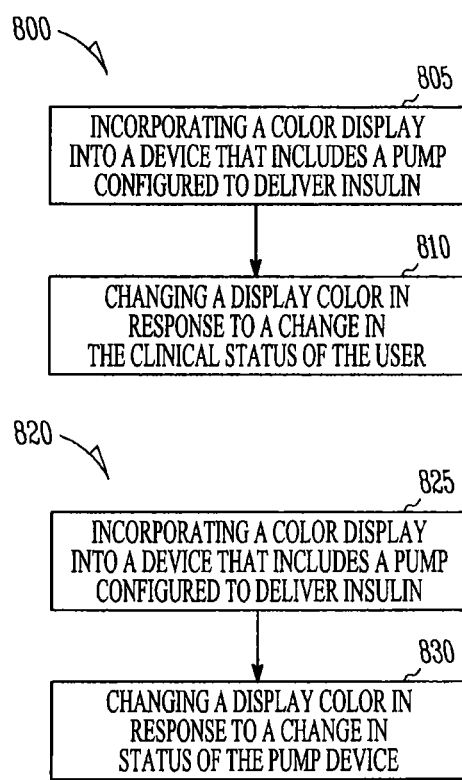
FIG. 8 shows a flow diagram of another method of presenting an insulin pump display to a user.

FIG. 8 shows a flow diagram of a method 800 of presenting an insulin pump display to a user. At block 805, a color display is incorporated into a device that includes a pump configured to deliver insulin. At block 810, a display color is changed in response to a change in clinical status of the user.

Returning to FIG. 7, according to some embodiments, the display module 725 is configured to change the color indication in response to a change in status of the insulin pump device. Examples of a change in status of the insulin pump device include, among other things, an insulin cartridge containing less than a threshold level of insulin, a device battery having a capacity less than a threshold battery capacity value, or an indication that the insulin pump device (e.g., the pump 705 itself) has stopped operating.

FIG. 8 also shows a flow diagram of a second method 820 of providing an insulin pump display to a user. At block 825, a color display is incorporated into a device that includes a pump configured to deliver insulin. In some embodiments, a color bistable display is incorporated into the device. At block 830, a display color is changed in response to a change in status of the insulin pump device.

Alternative Remote Display

Insulin pumps continue to decrease in size as technology advances. However, bigger displays are sometimes desirable for training on the devices or if the user has impaired vision.

Figure 9:
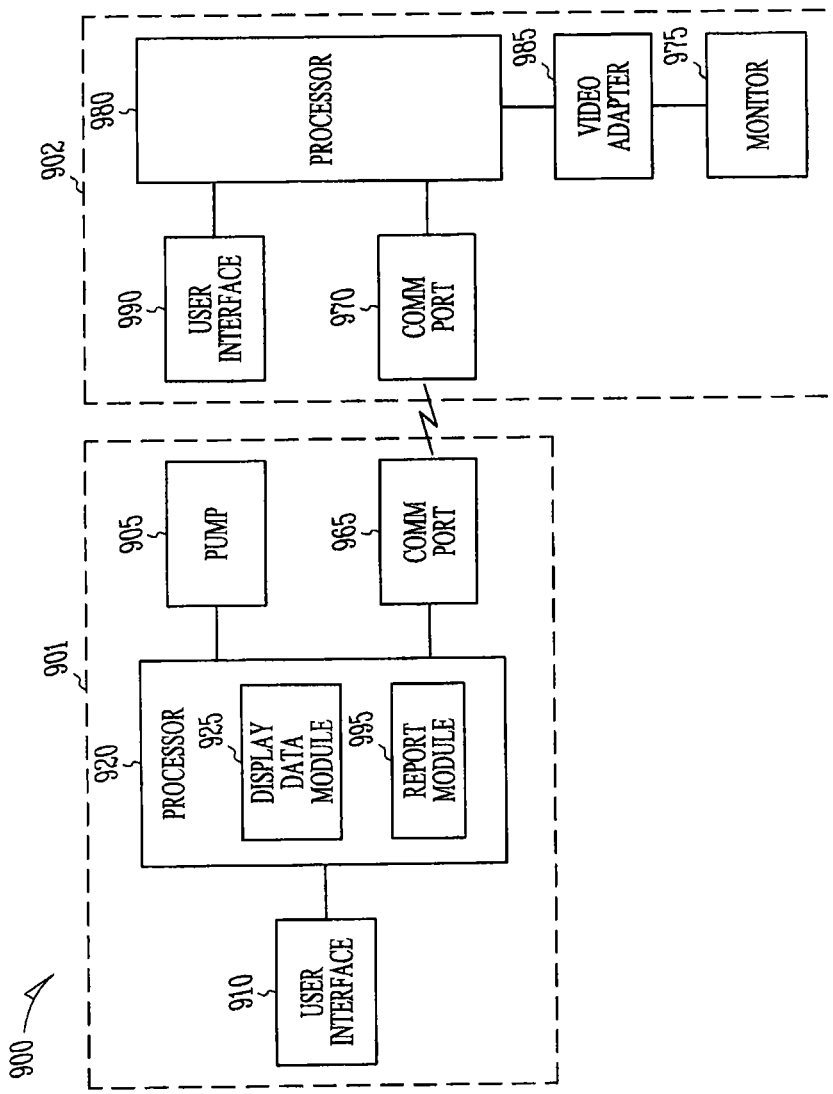
FIG. 9 is a block diagram of portions of an embodiment of system for providing a display for an insulin pump device.

FIG. 9 is a block diagram of portions of an embodiment of system 900 for providing a display for an insulin pump device. The system 900 comprises an insulin pump device 901 and a display device 902. The insulin pump device 901 includes a pump 905 configured to deliver insulin, a user interface 910, a communication port 965, and a first processor 920 communicatively coupled to the pump 905, the user interface 910, and the communication port 965.

The display device 902 includes a communication port 970, a monitor 975, and a second processor 980 communicatively coupled to the communication port 970 and the monitor 975. The first processor 920 includes a display data module 925 that communicates display information from the insulin pump device to the display device 902 via the communication ports 965, 970.

In some embodiments, the communication ports 965, 970 are wireless ports, such as an IR ports or RF ports for example. The insulin pump device 901 and the display device may communicate using a wireless protocol such as Bluetooth protocol, the WiFi protocol, or the infrared data (IrDA) protocol. In some embodiments, the communication ports 965 are wired ports, such as serial ports for example. The insulin pump device 901 and the display device may communicate using the universal serial bus (USB) protocol.

Input signals received at the user interface 910 change operation of the insulin pump device 901. These changes are reflected on the monitor 975 of the display device 902. The data display module 925 converts input received via the user interface 910 into changes to a display, and communicates updated display information according to the received input to the display device 902. The second processor receives the display information via the communication port 970 and displays a user menu for the insulin pump device 901 on the monitor 975.

Examples of display information communicated by the display data module 925 to the display device 902 include, among other things, an indication of status of the insulin pump device, a prompt to initiate a task by the insulin pump device, or an operation parameter of the insulin pump device. In some embodiments, the display data module 925 communicates, for display on the display device 902, instructions for using the insulin pump device 901. This is useful for training a new user to operate the insulin pump device 901.

The monitor 975 may be a larger display than is available for the insulin pump device 901, and the second processor 980 may display an enlarged version of the user menu for the insulin pump device 901 on the monitor 975. This allows the user to easily see how the input into the user interface 910 has effected operation of the insulin pump device 901. In some embodiments, the monitor 975 is a video monitor and the display device 902 includes a video adapter 985 communicatively coupled to the second processor 980 and the video monitor to convert the received display information to a video format for display on the video monitor.

According to some embodiments, the display device 902 includes a second user interface 990 communicatively coupled to the second processor 980. The second processor 980 manipulates the user menu for the insulin pump device 901 on the monitor 975 according to input received via the second user interface 990. Thus, the user menu displayed on the display device 902 may be changed according to input received via the second user interface 990. For example, the second user interface 990 allows the second processor to change a contrast of the user menu for the insulin pump device displayed on the monitor, a size of the user menu for the insulin pump device displayed on the monitor, or a color used in the displaying the user menu for the insulin pump device on the monitor.

According to some embodiments, the first processor 920 includes a report module 995 to generate a device report. As described previously, the device report may include historical insulin delivery information, recorded use parameters, and changes in the clinical status of the user. The display data module 925 communicates the device report to the display device 902 for display.

Figure 10:
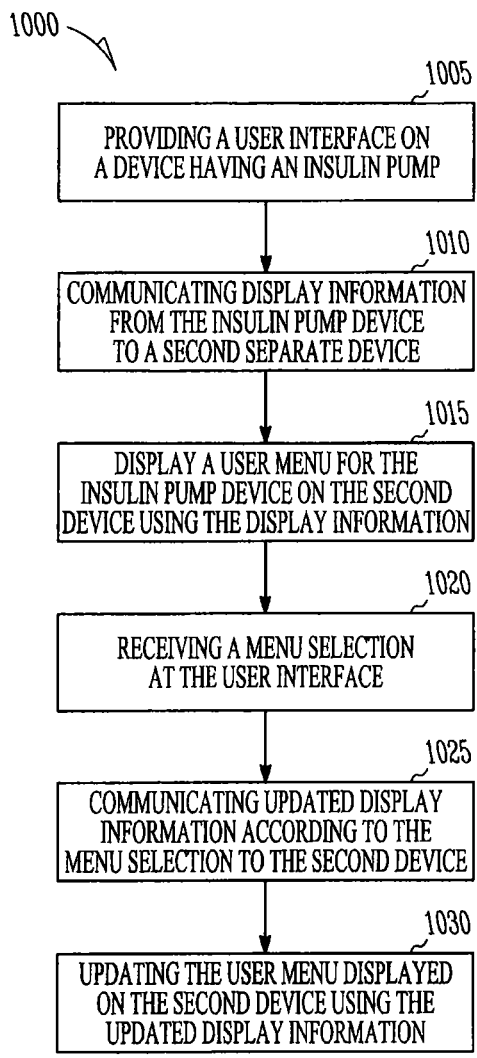
FIG. 10 is a flow diagram of another method of presenting a display for an insulin pump device.

FIG. 10 is a flow diagram of a method 1000 of presenting a display for an insulin pump device. At block 1005, a user interface is provided on a device having an insulin pump. At block 1010, display information is communicated from the insulin pump device to a second separate device. At block 1015, displaying a user menu for the insulin pump device is displayed on the second device using the display information. In some embodiments, the display information is converted to a video format at the second device and displayed on a video monitor. At block 1020, a menu selection is received at the user interface of the insulin pump. The menu selection is a menu item displayed on second device. The menu selection may be to change an operating parameter, initiate insulin therapy, display a device status, or run a device diagnostic for example. At block 1025, updated display information is communicated to the second device according to the menu selection.

Figure 11:
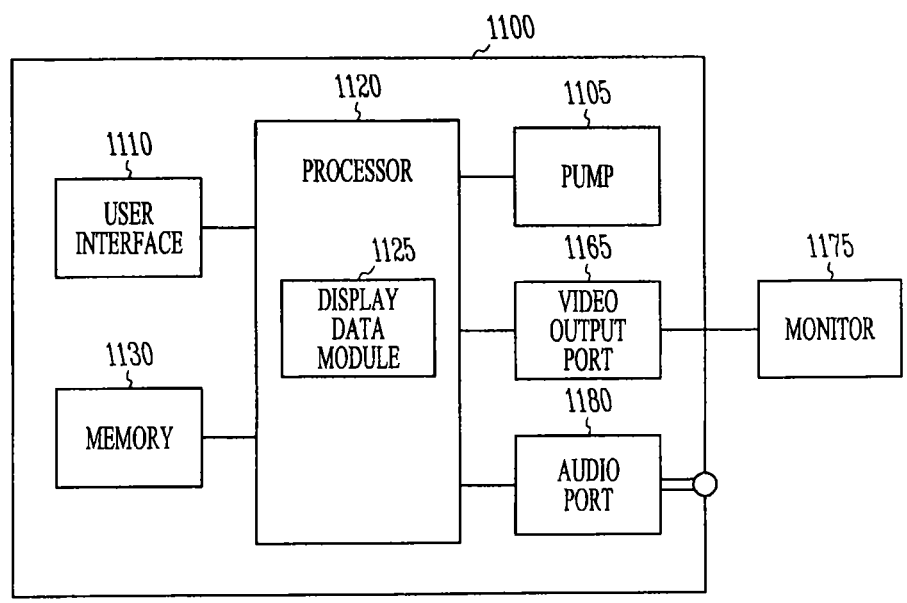
FIG. 11 is a block diagram of portions of an embodiment of an insulin pump device having an alternative display.

FIG. 11 is a block diagram of portions of an embodiment of an insulin pump device 1100 having an alternative display. The insulin pump device 1100 includes a pump 1105 configured to deliver insulin, a video output port 1165, and a processor 1120 communicatively coupled to the pump 1105 and the video output port 1165. The processor 1120 includes a display data module 1125 that communicates video display information via the video output port to a second separate device, such as a video monitor 1175 for example. The insulin pump device 100 is connected to the monitor 1175 via the video output port 1165.

In some embodiments, the video output port 1165 is an analog video output. The display data module 1125 provides the video display information in an analog video format at the video output port 1165. Examples of analog video formats provide by the display data module 1125 include, among other things, composite video, S video, component video, and VGA. In some embodiments, the video output port 1165 is a digital video output. The display data module 1125 provides the video display information in a digital format at the video output port 1165. Examples of digital video formats provide by the display data module 1125 include, among other things, High Definition Multimedia Interface (HDMI) and Digital Visual Interface (DVI).

In some embodiments, the insulin pump device 1100 includes a user interface 1110. The display data module 1125 converts input received via the user interface 1110 into changes to a display and communicates updated video display information according to the received input via the video output port. In this way, the monitor 1175 acts as a display for the insulin pump device 1100. The user interface 1110 may include a display screen on the insulin pump device 1100. The display data module 1125 may provide updated data to both the user interface display and the monitor 1175. The monitor 1175 may thereby function as an enlarged version of the device display screen.

In some embodiments, the insulin pump device 1100 includes a memory 1130. The memory 1130 stores one or more files containing video data. The display data module 1125 plays a video data file via the video output port 1165. The video data file may include training material, and the video data file provides a video tutorial to the user on the monitor 1175 when played. In some embodiments, the insulin pump device 1100 plays the video data file in response to an input received at the user interface 1110, such as an indication of menu selection for example.

In some embodiments, the insulin pump device 1100 includes an audio port 1180. The memory 1130 may store one or more files containing audio data. The display data module 1125 is configured to play the audio data file via the audio port 1180 in association with playing the video data file. In some embodiments, if the format of the file allows audio and video to be combined, the audio and video files may be provided by a single output port. The audio file may indicate a pump-related alarm or alert, or the audio file may accompany the training video.

Figure 12:
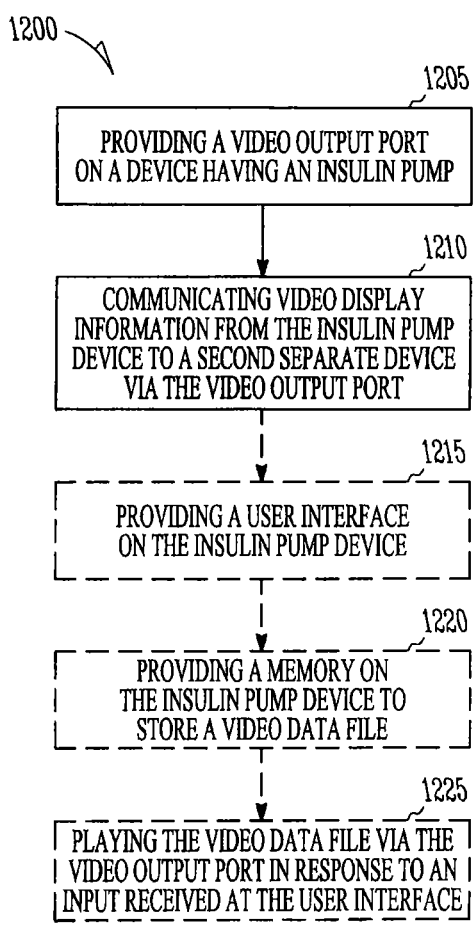
FIG. 12 is a flow diagram of another method of presenting a display for an insulin pump device.

FIG. 12 is a flow diagram of another method 1200 of presenting a display for an insulin pump device. At block 1205, a video output port is provided on a device having an insulin pump. At block 1210, video display information is communicated from the insulin pump device to a second separate device via the video output port. The second device may be a monitor or a television depending on the video format. Thus, the pump is a video driver for the second device.

As further shown in FIG. 12, in some embodiments the method 1200 includes, at block 1215, providing a user interface on the insulin pump device. At block 1220, providing a memory is provided on the insulin pump device to store one or more video data files. At block 1225, the video data file is played via the video output port in response to an input received at the user interface.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 CFR § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A medical infusion pump having a user interface configured to assist a user in operation of the medical infusion pump by automatically customizing display menus according to which functions are used most often, thereby improving operability of the pump for users suffering from a medical condition, the medical infusion pump comprising:
   a pump configured to deliver medicament to the user; and
   a user interface including a processor and a display, the user interface configured to present a plurality of display menus, each display menu having at least one menu item presented on the display, wherein a selection of a menu item by the user causes the processor to perform an action associated with the selected menu item, and wherein the processor tracks the selection of menu items and arranges at least one of the plurality of display menus and/or the menu items into a presentation order according to a frequency with which the menu items are selected, wherein arranging at least one of the plurality of display menus and/or menu items into the presentation order according to a frequency with which the menu items are selected includes moving menu items selected most often closer to a beginning of the presentation order, and
   further wherein after a user frequently selects a menu item not on a home menu, an icon relating to the menu item is added to the home menu for display on the home menu.

2. The medical infusion pump of claim 1, wherein if a user frequently selects a menu item on a therapy delivery display menu, the processor automatically moves the therapy delivery display menu higher in a hierarchy of the plurality of display menus.

3. The medical infusion pump of claim 1, wherein the processor includes menu items in a home menu for display on the user interface according to user preference information, wherein the menu items included in the home menu are a subset of all menu items on all of the plurality of display menus.

4. The medical infusion pump of claim 3, wherein the home menu includes an icon to indicate an amount of medicament remaining in the medical infusion pump.

5. The medical infusion pump of claim 3, wherein the home menu includes an icon to indicate a remaining battery life of the medical infusion pump.

6. The medical infusion pump of claim 3, wherein the processor reverts to display the home menu on the user interface when no menu items on a display menu are selected within a user-defined reversion time period.

7. The medical infusion pump of claim 1, wherein if the menu items relates to how much medicament is remaining in the medical infusion pump, an icon representing the medicament remaining in the medical infusion pump is added to the home menu for display on the user interface.

8. A medical infusion pump having a user interface configured to assist a user in operation of the medical infusion pump by automatically customizing display menus according to which functions are used most often, thereby improving operability of the pump for users suffering from a medical condition, the medical infusion pump comprising:
   a pump configured to deliver medicament to the user; and
   a user interface including a processor and a display, the user interface configured to present a plurality of display menus, each display menu having a plurality of menu items presented on the display, wherein a selection of a menu item by the user causes the processor to perform an action associated with the selected menu item, and wherein the processor tracks the selection of menu items and arranges the menu items within a display menu into a presentation order according to a frequency with which the menu items are selected, wherein arranging the menu items into the presentation order according to a frequency with which the menu items are selected includes moving menu items selected most often closer to a beginning of the presentation order, and further wherein after a user frequently selects a menu item not on a home menu, an icon relating to the menu item is added to the home menu for display on the home menu.

9. The medical infusion pump of claim 8, wherein the plurality of display menus include a home screen.

10. The medical infusion pump of claim 9, wherein the menu items included in the home screen are a subset of all menu items on all of the plurality of display menus, and wherein the processor arranges the menu items within the home screen into a presentation order according to a frequency with which the menu items are selected.

11. The medical infusion pump of claim 9, wherein the home screen includes an icon to indicate an amount of medicament remaining in the medical infusion pump.

12. The medical infusion pump of claim 9, wherein the home screen includes an icon to indicate a remaining battery life of the medical infusion pump.

13. The medical infusion pump of claim 9, wherein the processor reverts to display the home screen on the user interface when no menu items on a display menu are selected within a user-defined reversion time period.

14. The medical infusion pump of claim 8, wherein if a user frequently selects a menu item on a therapy delivery display menu, the processor automatically moves the therapy delivery display menu higher in a hierarchy of the plurality of display menus.

15. The medical infusion pump of claim 8, wherein if the menu items relates to how much medicament is remaining in the medical infusion pump, an icon representing the medicament remaining in the medical infusion pump is added to the home menu for display on the user interface.

* * * * *